(12) United States Patent
Fedorov et al.

(10) Patent No.: US 7,704,743 B2
(45) Date of Patent: Apr. 27, 2010

(54) ELECTROSONIC CELL MANIPULATION DEVICE AND METHOD OF USE THEREOF

(75) Inventors: Andrei G. Fedorov, Atlanta, GA (US); Fahrettin L. Degertekin, Decatur, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 719 days.

(21) Appl. No.: 11/277,662

(22) Filed: Mar. 28, 2006

(65) Prior Publication Data

US 2006/0223185 A1 Oct. 5, 2006

Related U.S. Application Data

(60) Provisional application No. 60/666,661, filed on Mar. 30, 2005.

(51) Int. Cl.
*C12N 15/87* (2006.01)

(52) U.S. Cl. .................. 435/461; 435/285.2; 435/173.5; 435/173.6

(58) Field of Classification Search .................. None
See application file for complete search history.

(56) References Cited

U.S. PATENT DOCUMENTS

| 5,019,034 | A | 5/1991 | Weaver et al. |
|---|---|---|---|
| 5,318,514 | A | 6/1994 | Hofmann |
| 5,445,611 | A | 8/1995 | Eppstein et al. |
| 5,458,140 | A | 10/1995 | Eppstein et al. |
| 5,582,586 | A | 12/1996 | Tachibana et al. |
| 6,199,554 | B1 | 3/2001 | Mann et al. |
| 6,508,785 | B1 | 1/2003 | Eppstein |
| 6,527,716 | B1 | 3/2003 | Eppstein |
| 6,575,956 | B1 | 6/2003 | Brisken et al. |
| 6,821,264 | B1 | 11/2004 | Khurana et al. |
| 2002/0099356 | A1 | 7/2002 | Unger et al. |
| 2003/0009153 | A1 | 1/2003 | Brisken et al. |
| 2003/0078227 | A1 | 4/2003 | Greenleaf et al. |
| 2003/0229331 | A1 | 12/2003 | Brisken et al. |
| 2004/0001809 | A1 | 1/2004 | Brisken et al. |
| 2004/0033589 | A1 | 2/2004 | O'Brien |
| 2004/0045048 | A1 | 3/2004 | Liou |
| 2004/0192044 | A1 | 9/2004 | Degertekin et al. |
| 2005/0054208 | A1 | 3/2005 | Fedorov et al. |
| 2005/0064578 | A1 | 3/2005 | Muller-Hartmann et al. |
| 2005/0150015 | A1 | 7/2005 | Kasukabe et al. |
| 2006/0188992 | A1* | 8/2006 | Hagio et al. ................. 435/461 |

FOREIGN PATENT DOCUMENTS

| JP | 58107183 A | | 6/1983 |
|---|---|---|---|
| WO | WO 92/06185 | * | 4/1992 |
| WO | WO 00/63408 | | 10/2000 |

OTHER PUBLICATIONS

Miller et al., Somat. Cell Mol. Genet. vol. 27, (2002), pp. 115-134.*
Khine, Michelle, et al., "A single cell electroporation chip," Lab on a Chip, 2005, pp. 38-43.

* cited by examiner

*Primary Examiner*—James S Ketter
(74) *Attorney, Agent, or Firm*—Bryan W. Bockhop; Bockhop & Associates, LLC

(57) ABSTRACT

In method of injecting a substance into a living cell having a cell membrane, the substance, the cell and a liquid are placed into a tapering passage. Energy is applied to the cell, thereby inducing poration. To sort cells, a cellular suspension is placed in a tapering passage, including a narrow end that defines an opening that has a dimension corresponding to a cell size. An acoustic wave is applied, thereby forcing cells having a cell size smaller than the selected cell size through the opening, with a portion of the cells having a cell size not smaller than the selected cell size not forced through the opening. To extract material from a cell, an electric field and an acoustic wave are applied, thereby causing the cell membrane to allow the material to pass out of the cell.

14 Claims, 16 Drawing Sheets

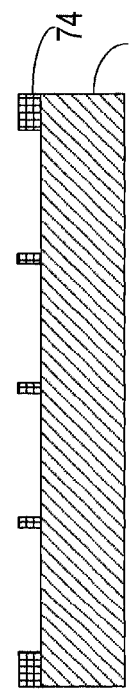
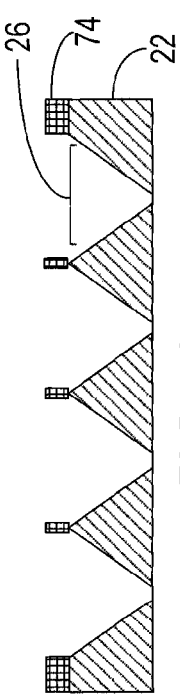
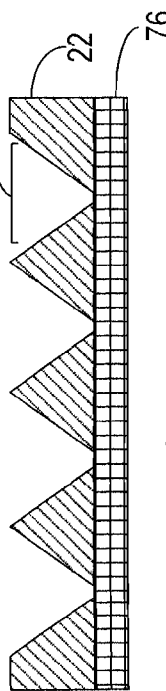
FIG. 4A  FIG. 4B  FIG. 4C  FIG. 4D
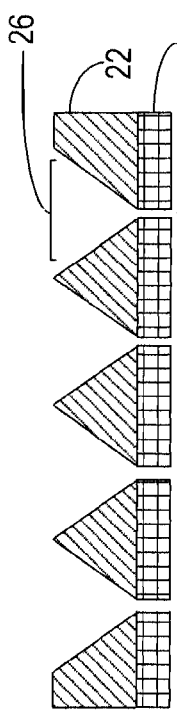
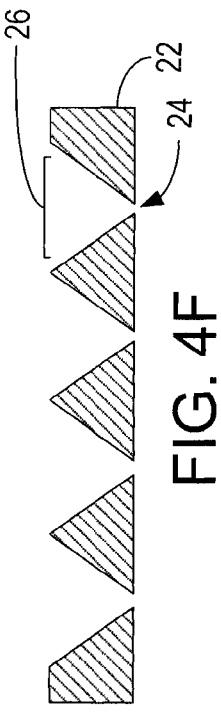
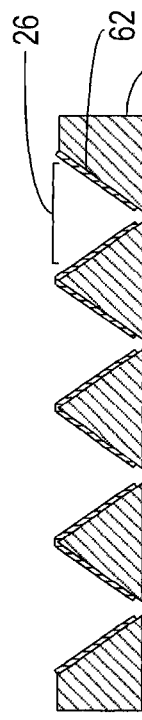
FIG. 4E  FIG. 4F  FIG. 4G  FIG. 4H

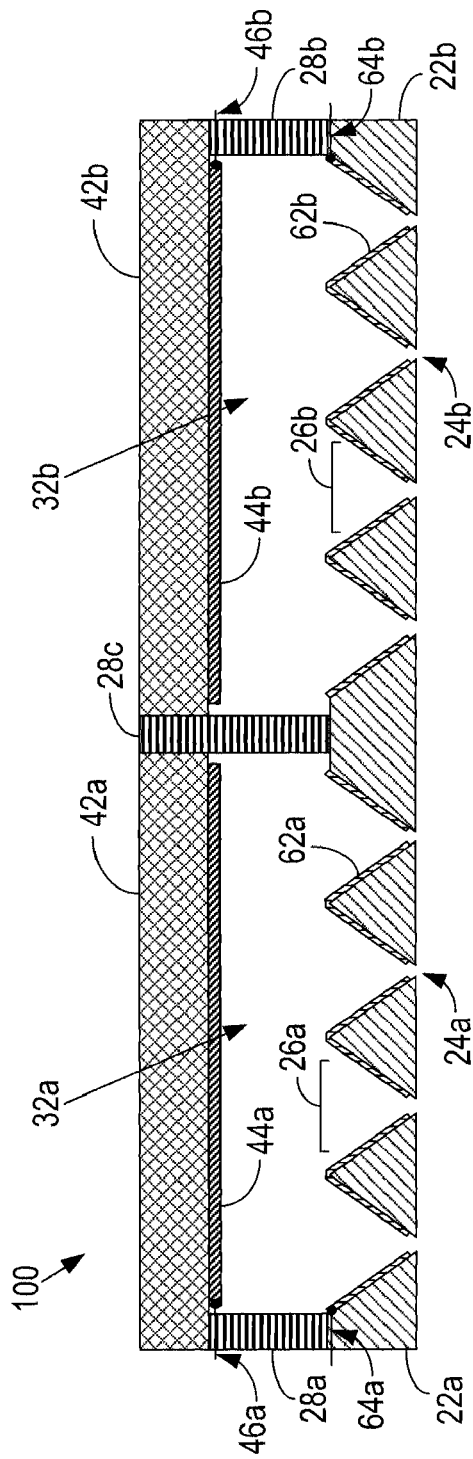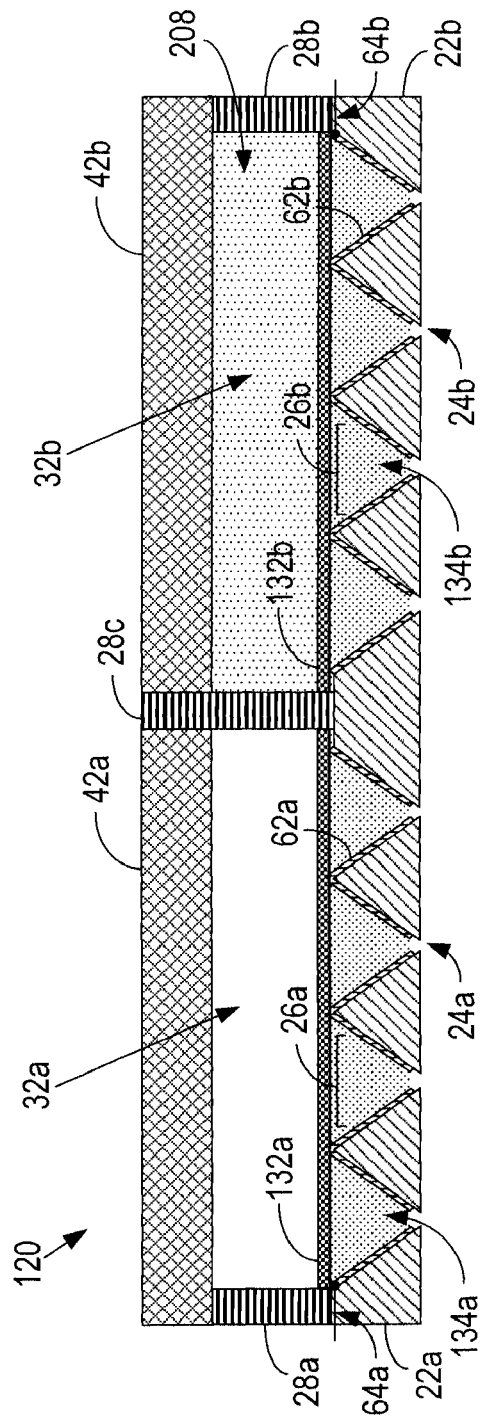

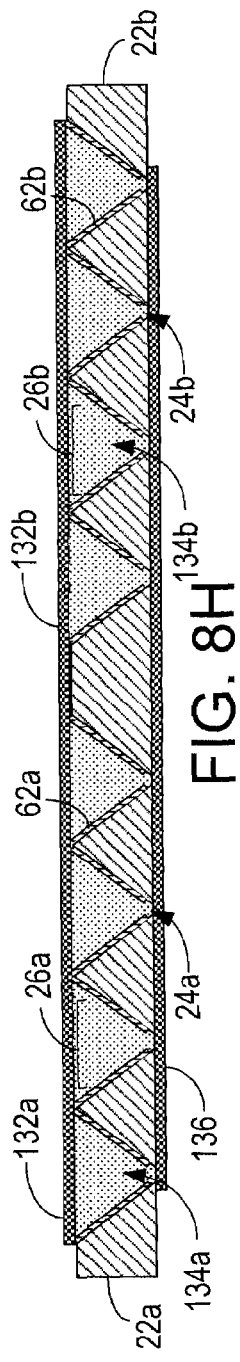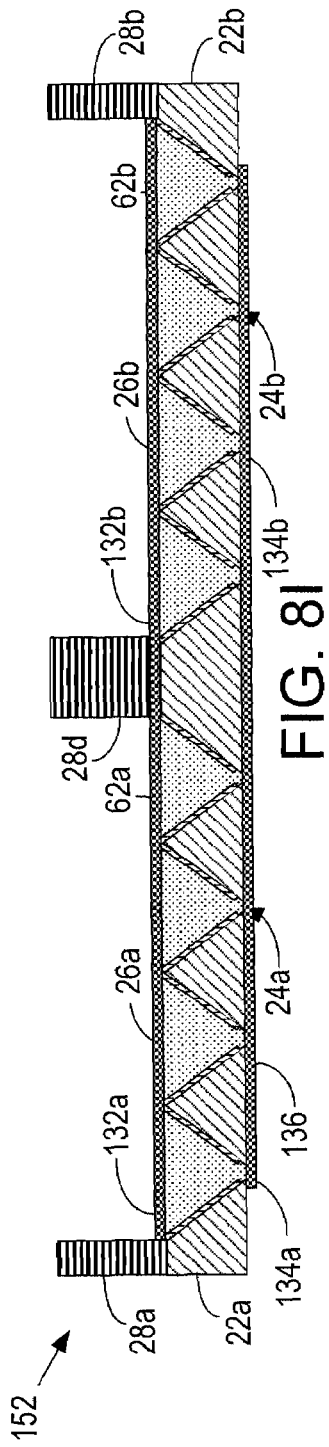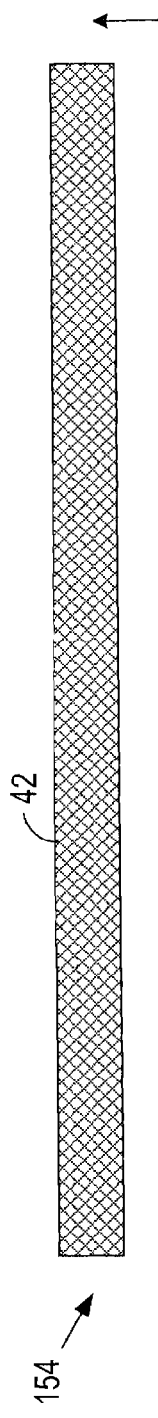

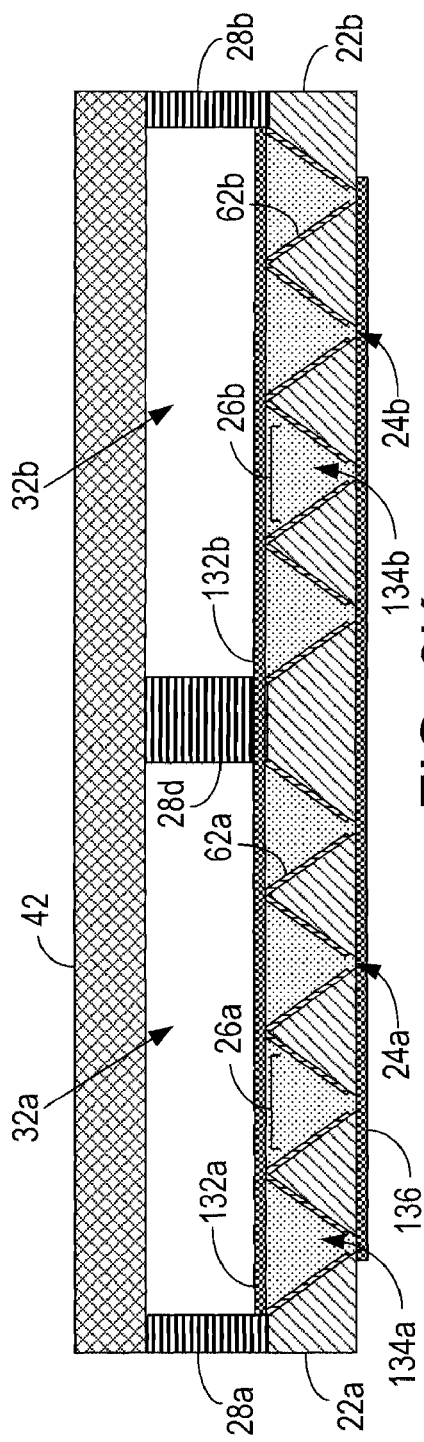
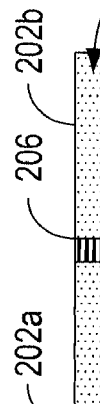
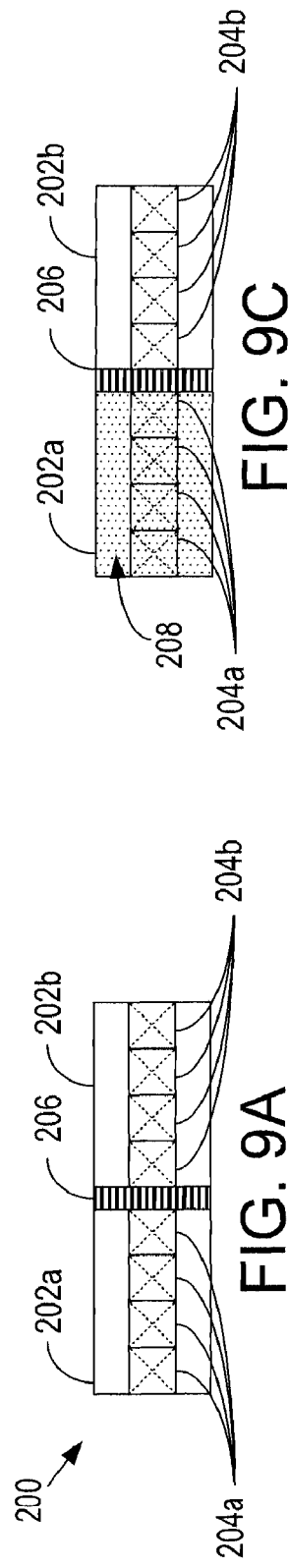
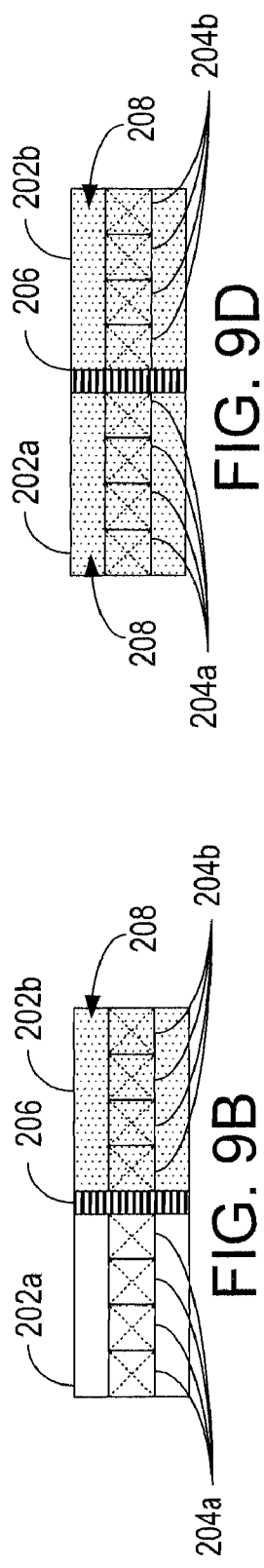

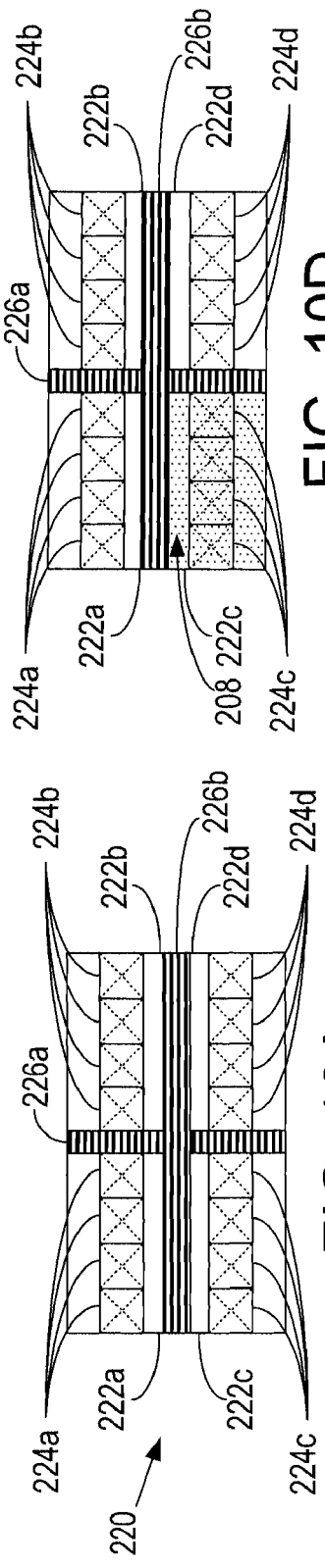
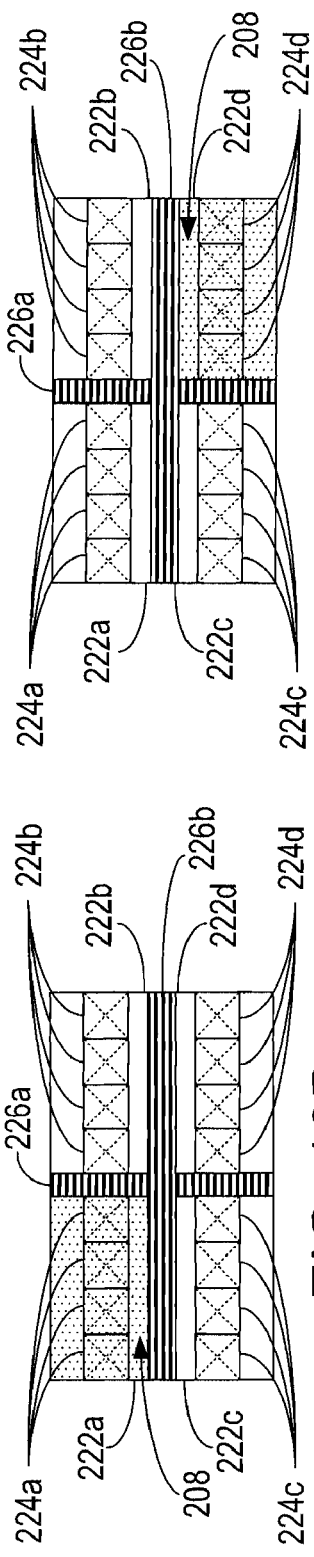
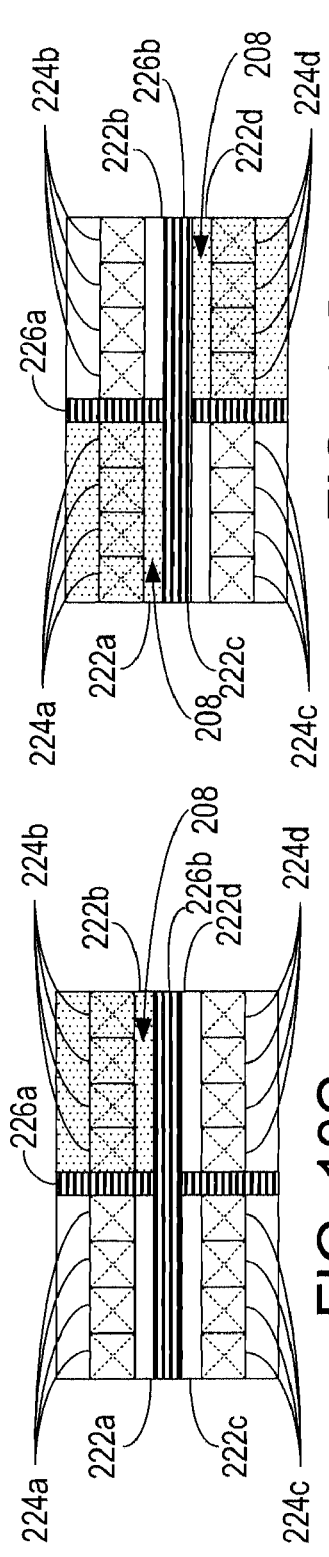
FIG. 10A   FIG. 10B   FIG. 10C
FIG. 10D   FIG. 10E   FIG. 10F

ELECTROSONIC CELL MANIPULATION DEVICE AND METHOD OF USE THEREOF

CROSS-REFERENCE TO RELATED APPLICATION

This application claims the benefit of U.S. Provisional Patent Application Ser. No. 60/666,661, filed Mar. 30, 2005, the entirety of which is hereby incorporated herein by reference.

BACKGROUND OF THE INVENTION

1. Field of the Invention

The present invention relates to cellular manipulation devices and, more specifically, to a device that can perform poration, transfection, lysis and sorting of living cells.

2. Description of the Prior Art

As reflected in the recent Proteomics special feature article ("Automated NanoElectrospray: A New Advance for Proteomics Researchers," Laboratory News, 2002) Mass Spectrometry (MS) has become the technology of choice to meet today's unprecedented demand for accurate bioanalytical measurements, including protein identification. Although MS can be used to analyze biomolecules with very large molecular weights (up to several MegaDaltons (Mda)), these molecules must be first converted to gas-phase ions before they can be introduced into a mass spectrometer for analysis. Electrospray ionization (ESI) has proven to be an enormous breakthrough in structural biology because it provides a mechanism for transferring large biological molecules into the gas phase as intact charged ions. It is the creation of efficient conversion of a very small quantity of a liquid sample (proteins are very expensive and often very difficult to produce in sizable quantities) into gas-phase ions that is one of the main bottlenecks for using mass spectrometry in high throughput proteomics.

Conventional (micro and nano) capillary ESI sources, as well as the more recently developed MEMS-based electrospray devices, rely on application of strong electric field, which is used for focusing of the charged jet leading to jet tip instabilities and formation of small droplets of the analyte sample. As a result, the size and homogeneity of the formed droplets is determined by the magnitude and geometry of the applied electric field, thus requiring high voltages for generating sufficiently small micrometer or sub-micrometer droplets via the so-called Taylor cone nebulization. Reliance on the electrohydrodynamic Taylor cone focusing of the jet to form the mist of sufficiently small charged droplets leading to single ion formation imposes several fundamental and significant limitations on the capabilities of the conventional ESI interface.

One such problem is that a very large electric potential needs to be applied to the capillary tip (up to a few kilovolts relative to the ground electrode of the MS interface) to ensure formation of the stable Taylor cone, especially at higher flow rates and with poorly conducting organic solvents.

An additional problem is that the choice of suitable solvents is very much restricted to those featuring high electrical conductivity and sufficiently low surface tension. This restriction imposes severe limitations on the range of biological molecules that can be analyzed via ESI Mass Spectrometry. For example, use of pure water (the most natural environment for most biomolecules) as a solvent is difficult in conventional ESI since the required onset electrospray voltage is greater than that of the corona discharge, leading to an unstable Taylor cone, damage to the emitter and uncontrollable droplet/ion formation.

Since the conventional ESI relies on the disintegration of the continuous jet emanating from the Taylor cone into an aerosol of charged droplets, there is the limit to the lowest flow rate (and therefore the minimum sample size) that can be used during the analysis. For example, commercial products require the minimum sample volume to be about 3 μL.

Another problem is that sample utilization (i.e., fraction of the sample volume that is introduced and being used in MS analysis relative to the total volume of the electrosprayed sample) is very low due to uncontrollable nature of electrohydrodynamic atomization process that relies on the surface instabilities. Further, a significant dead volume (i.e., a fraction of the sample that cannot be pulled from the capillary by electrical forces) is unavoidable in any jet-based atomization process.

Still other problems are that commercially available ESI devices are very expensive because of the manufacturing difficulties, and limited usable lifetime because of the high voltage operation in a chemically-aggressive solvent environment.

An ability to extract DNA from or inject DNA into living cells is critical to any genetic, molecular biology, drug design and delivery, and pharmaceutical research and development work. Drug delivery, pharmaceutical, and biotech industries routinely need to be able to extract DNA from and inject DNA into a cell. This is probably the most critical step in many molecular biology and genetics modification protocols currently used.

Some methods of injecting DNA into cells involve poration of a group of cells. In poration, the cells are subjected to an energy field that causes pores in the cell membranes to dilate. Typically, many cells are placed in a field that varies spatially and those cells that are in the area of a certain field strength porate, while the rest do not. The low level of predictability and accuracy of poration results in a low yield and the inefficiency of requiring the technician to spend extra time sorting cells that have successfully porated from those that have not successfully porated.

Therefore, there is a need for a system for extracting and injecting materials into living cells with a high level of predictability and accuracy.

SUMMARY OF THE INVENTION

The disadvantages of the prior art are overcome by the present invention which, in one aspect, is a method of injecting a substance into a living cell having a cell membrane. The substance, the cell and a liquid are placed into a tapering passage. An energy is applied to the cell sufficient to induce poration of the cell.

In another aspect, the invention is a method of sorting cells, in which the cells are suspended in a liquid, thereby creating a cellular suspension. The cellular suspension is placed in a tapering passage. The tapering passage includes a wide end and an oppositely-disposed narrow end that defines an opening, with the opening having a dimension corresponding to a selected cell size. A standing acoustic wave is applied to the cells, thereby forcing cells having a cell size smaller than the selected cell size through the opening and so that at least a portion of the cells having a cell size not smaller than the selected cell size are not forced through the opening.

In another aspect, the invention is a method of extracting material from a cell, having a cell membrane, in which the cell is suspended in a liquid, thereby creating a cellular suspension. A predetermined electric field is applied to the cell. An acoustic wave is applied to the cell. The electric field and the acoustic wave cause the cell membrane to allow the material to pass out of the cell.

In yet another aspect, the invention is an apparatus for manipulating cells that includes a substrate, a first poration electrode, a second poration electrode, a fluid driving structure and an oscillating circuit. The substrate has a first side and an opposite second side and defines at least one tapering passage passing therethrough. The tapering passage opens to the first side with a wide end and also opens to the second side with a narrow end. The narrow end has a size that corresponds to a predetermined characteristic of a selected cell. The first poration electrode is spaced-apart from the second poration electrode and is disposed so as to impart a predetermined electrical field on the passage when an electrical potential is applied between the first poration electrode and the second poration electrode. The fluid driving structure drives fluid through the opening. The oscillating circuit applies an oscillating potential to the ultrasonic transducer, thereby causing the ultrasonic transducer to generate a standing wave in the tapering passage. The standing wave and the electrical field impart energy on at least a portion of the cells so as to cause a predetermined action on the cells.

A device for on-demand DNA delivery in or out of the cell via a combination (or possibly individual action) of ultrasonic and electrical poration or lysis, respectively, of the cell membrane is disclosed. In addition to poration and lysing functionality, the device also includes the capability of in-line size selective cell sorting (via control of the ejector nozzle size) prior to poration or lysis. It also enables transport of modified cell DNA to a final destination as a post-poration/lysis step for further processing. The device can operate in both high-throughput and multiplexed mode in the microarray format.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

BRIEF DESCRIPTION OF THE FIGURES OF THE DRAWINGS

FIGS. 4A through 4J are illustrations of cross-sections of a representative embodiment of a method of forming the electrospray system shown in FIG. 3.

FIG. 5 is an illustration of a cross-section of another embodiment of an electrospray system, as shown in FIG. 1.

FIG. 6 is an illustration of a cross-section of another embodiment of an electrospray system, as shown in FIG. 1.

FIGS. 8A through 8K are illustrations of cross-sections of a representative embodiment of a method of forming the electrospray system shown in FIG. 7.

FIGS. 9A through 9D are illustrations of top views of representative embodiments of an electrospray system. FIG. 9B illustrates an acoustically responsive fluid bubble in one section of the electrospray system, while FIG. 9C illustrates a fluid bubble in the other section of the electrospray system.

FIGS. 10A through 10F are illustrations of top views of representative embodiments of an electrospray system. FIGS. 10B through 10F illustrate an acoustically responsive fluid bubble being positioned from one section of the electrospray system to another.

DETAILED DESCRIPTION OF THE INVENTION

Figure 1:
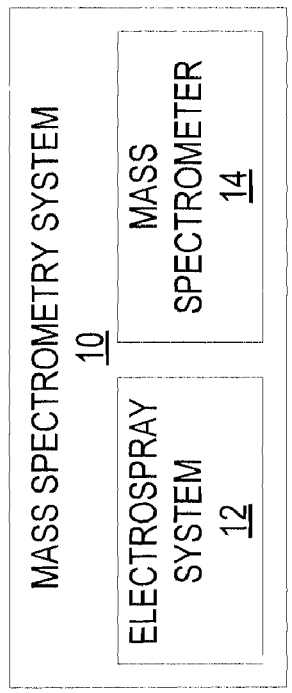
FIG. 1 is a schematic of a representative embodiment of a mass spectrometry system

A preferred embodiment of the invention is now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on."

Mass spectrometry systems, methods of use thereof, electrospray systems, methods of use thereof, and methods of fabrication thereof, are disclosed. The mass spectrometry systems can be operated in a high throughput (parallel) and/or a multiplexed (individually controlled) mode. The mass spectrometry systems described herein include embodiments of electrospray systems that are capable of independently forming a fluid aerosol (i.e., droplets) and ionizing the molecules present in the fluid. The droplets are formed by producing resonant ultrasonic waves (e.g., acoustical pressure waves) within a reservoir interfaced with a structure having shaped cavities (e.g., acoustic horns) that focus the ultrasonic waves and thus amplify the pressure and form a pressure gradient at an ejector nozzle for each shaped cavity. The high pressure gradient close to the ejector nozzle accelerates fluid droplets of size comparable to the ejector nozzle diameter (e.g., a few micrometers) out of the ejector nozzle, which are thus controllably generated (e.g., ejected) during every cycle of the drive signal (e.g., a sinusoidal signal) after an initial transient. In other words, the droplets are produced either discretely (e.g., drop-on-demand), or as a continuous jet-based approach.

Decoupling of the droplet generation and the molecular ionization reduces the energy required to ionize the molecules and also lowers the sample size required, minimizes the dead volume, and improves sample utilization. In addition, decoupling of the droplet generation and the molecular ionization enables the electrospray system to produce droplets including ionized molecules at low voltages (e.g., about 80 to a few hundred Volts (V)), in contrast to commonly used electrospray systems (e.g., 1 kV to several kV). In addition, relatively small volumes of fluids (e.g., about 100 nanoliters (nL) to a few hundred nL) can be used in contrast to commonly used electrospray systems (e.g., 3 µL or more).

Embodiments of the electrospray system can be used in a continuous flow online operation (e.g., continuous loading of samples) and/or in discrete off-line operation. In discrete off-line operation, embodiments of the electrospray system can include a disposable nozzle system (e.g., array of nozzle systems that can include one or more samples and standards) that can be charged with one or more fluids and inserted into the electrospray system. The disposable nozzle system can be removed and replaced with another disposable nozzle system.

Additional embodiments of the electrospray system can be used in a high throughput electrospray system (e.g., simultaneous use of nozzles) and/or in a multiplexed electrospray system (e.g., using an array of individually addressable nozzles or individually addressable groups of nozzles). Details describing each of these embodiments are described in more detail below.

FIG. 1 is a schematic of a representative embodiment of a mass spectrometry system 10. The mass spectrometry system 10 includes an electrospray system 12 and a mass spectrometer 14. The electrospray system 12 is interfaced with the mass spectrometer 14 so that the fluid sample (e.g., in the form of droplets) is communicated from the electrospray system 12 to the mass spectrometer system 14 using electrostatic lenses and the like under one or more different vacuum pressures. In addition, the electrospray system 12 can be also interfaced with a liquid chromatography system, a fluidic system for selective delivery of different samples, and automated fluid charging system such as a pump, for example.

The mass spectrometer 14 can include, but is not limited to, a mass analyzer and an ion detector. The mass analyzer can include, but is not limited to, a time-of-flight (TOF) mass analyzer, an ion trap mass analyzer (IT-MS), a quadrupole (Q) mass analyzer, a magnetic sector mass analyzer, or an ion cyclotron resonance (ICR) mass analyzer. In some embodiments, because it can be used to separate ions having very high masses, the mass analyzer is a TOF mass analyzer.

The ion detector is a device for recording the number of ions that are subjected to an arrival time or position in a mass spectrometry system 25, as is known by one skilled in the art. Ion detectors can include, for example, a microchannel plate multiplier detector, an electron multiplier detector, or a combination thereof. In addition, the mass spectrometry system 10 includes vacuum system components and electronic system components, as are known by one skilled in the art.

In general, the electrospray system 12 is capable of independently forming a fluid aerosol (i.e., droplets) and ionizing the molecules present in the fluid. The ionized molecules are then mass analyzed by the mass spectrometer 14, which can provide information about the types of molecules present in the fluid sample.

Figure 2:
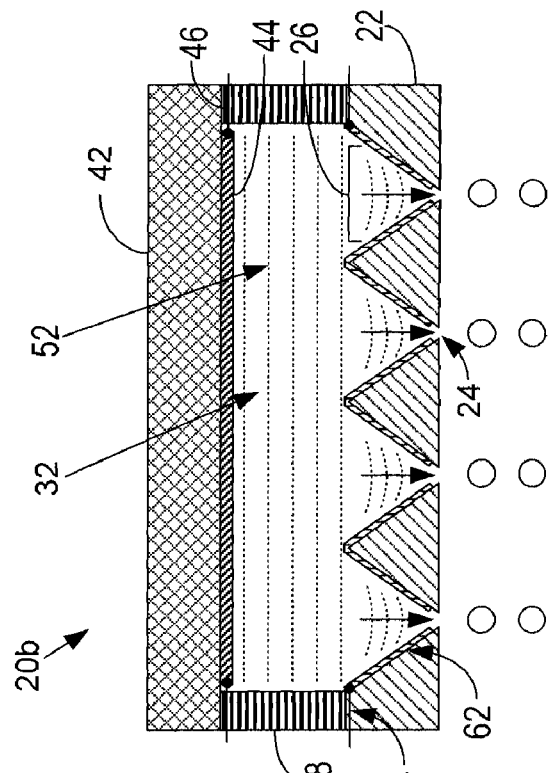
FIG. 2 is a FIG. 1 is an illustration of a cross-section of an embodiment of an electrospray system, as shown in FIG. 1.

FIG. 2 is an illustration of a cross-section of an embodiment of an electrospray system 20a, as shown in FIG. 1. The electrospray system 20a includes, but is not limited to, an array structure 22 including ejector structures 26, a separating layer 28, a reservoir 32, an actuator 42, and an ionization source 44. A fluid can be disposed in the reservoir 32 and in the array 22 of ejector structures 26. Upon actuation of the actuator 42, a resonant ultrasonic wave 52 can be produced within the reservoir 32 and fluid. The resonant ultrasonic wave 52 couples to and transmits through the liquid and is focused by the ejector structures 26 to form a pressure gradient 54 within the ejector structure 26. The high-pressure gradient 54 accelerates fluid out of the ejector structure 26 to produce droplets 56. The cycle of the drive signal applied to the actuator 42 dictates, at least in part, the rate at which the droplets are discretely produced.

A drop-on-demand ejection can be achieved by modulation of the actuation signal in time domain. The actuator 42 generating ultrasonic waves can be excited by a finite duration signal with a number of sinusoidal cycles (a tone burst) at the desired frequency. Since a certain energy level is reached for droplet ejection, during the initial cycles of this signal, the standing acoustic wave pattern in the resonant cavity is established and the energy level is brought up to the ejection threshold. The number of cycles required to achieve the threshold depends on the amplitude of the signal input to the wave generation device and the quality factor of the cavity resonance. After the threshold is reached, one or more droplets can be ejected in a controlled manner by reducing the input signal amplitude after the desired number cycles. This signal can be used repetitively, to eject a large number of droplets. Another useful feature of this operation is to reduce the thermal effects of the ejection, since the device can cool off when the actuator 42 is turned off between consecutive ejections. The ejection speed and droplet size can also be controlled by the amplitude and duration of the input signal applied to the actuator 42.

The array structure 22 can include, but is not limited to, an ejector nozzle 24 and an ejector structure 26. In general, the material that the array structure 22 is made of has substantially higher acoustic impedance as compared to the fluid. The array structure 22 can be made of materials such as, but not limited to, single crystal silicon (e.g., oriented in the (100), (010), or (001) direction), metals (e.g., aluminum, copper, and/or brass), plastics, silicon oxide, silicone nitride, and combinations thereof.

The ejector structure 26 can have a shape such as, but not limited to, conical, pyramidal, or horn-shaped with different cross-sections. In general, the cross-sectional area is decreasing (e.g., linear, exponential, or some other functional form) from a base of the ejector nozzle 26 (broadest point adjacent the reservoir 32) to the ejector nozzle 24. The cross sections can include, but are not limited to, a triangular cross-section (as depicted in FIG. 2), and exponentially narrowing. In an embodiment, the ejector structure 26 is a pyramidal shape.

The ejector structure 26 has acoustic wave focusing properties in order to establish a highly-localized, pressure maximum substantially close to the ejector nozzle 24. This results in a large pressure gradient at the ejector nozzle 24 since there is effectively an acoustic pressure release surface at the ejector nozzle 24. Since the acoustic velocity is related to the pressure gradient through Euler's relation, a significant momentum is transferred to the fluid volume close to the ejector nozzle 24 during each cycle of the acoustic wave in the ejector structure 26. When the energy coupled by the acoustic wave in the fluid volume is substantially larger than the restoring energy due to surface tension, viscous friction, and other sources, the fluid surface is raised from its equilibrium position. Furthermore, the frequency of the waves should be such that there is enough time for the droplet to break away from the surface due to instabilities.

The ejector structure 26 has a diameter (at the base) of about 50 micrometers to 5 millimeters, 300 micrometers to 1 millimeter, and 600 micrometers to 900 micrometers. The distance (height) from the ejector nozzle 24 to the broadest point in the ejector structure 26 is from about 20 micrometers to 4 millimeters, 200 micrometers to 1 millimeter, and 400 micrometers to 600 micrometers.

The ejector nozzle 24 size effectively determines the droplet size and the amount of pressure focusing along with the ejector structure 26 geometry (i.e., cavity geometry). The ejector nozzle 24 can be formed using various micromachining techniques as described below and can have a shape such as, but not limited to, circular, elliptic, rectangular, and rhombic. The ejector nozzle 24 has a diameter of about 50 nanometers to 50 micrometers, 200 nanometers to 30 micrometers, and 1 micrometer to 10 micrometers.

In one embodiment all of the ejector nozzles are positioned inline with a mass spectrometer inlet, while in another embodiment only select ejector nozzles (1 or more) are positioned inline with the mass spectrometer inlet.

The array structure 22 can include one ejector nozzle 24 (not shown), a (one-dimensional) array of ejector nozzles 24, or a (two dimensional) matrix of parallel arrays of ejector nozzles 24. As shown in FIG. 2, the ejector structure 26 can include one ejector nozzle 24 each or include a plurality of ejector nozzles 24 in a single ejector structure 26.

The separating layer 28 is disposed between the array structure 22 and the actuator 46. The separating layer 28 can be fabricated of a material such as, but not limited to, silicon, metal, and plastic. The separating layer 28 is from about 50 micrometers to 5 millimeters in height (i.e., the distance from the actuator 42 to the array structure 22), from about 200 micrometers to 3 millimeters in height, and from about 500 micrometers to 1 millimeter in height.

The reservoir 32 is substantially defined by the separating layer 28, the array structure 22, and the actuator 42. In general, the reservoir 32 and the ejector structures 26 include the fluid. The reservoir 32 is an open area connected to the open area of the ejector structures 26 so that fluid flows between both areas. In addition, the reservoir 32 can also be in fluidic communication (not shown) with a liquid chromatography system or other microfluidic structures capable of flowing fluid into the reservoir 32.

In general, the dimensions of the reservoir 32 and the ejector structure 26 can be selected to excite a cavity resonance in the electrospray system at a desired frequency. The structures may have cavity resonances of about 100 kHz to 100 MHz, depending, in part, on fluid type and dimensions and cavity shape, when excited by the actuator 42.

The dimensions of the reservoir 32 are from 100 micrometers to 4 centimeters in width, 100 micrometers to 4 centimeters in length, and 100 nanometers to 5 centimeters in height. In addition, the dimensions of the reservoir 32 are from 100 micrometers to 2 centimeters in width, 100 micrometers to 2 centimeters in length, and 1 micrometer to 3 millimeter in height. Further, the dimensions of the reservoir 32 are from 200 micrometers to 1 centimeters in width, 200 micrometers to 1 centimeters in length, and 100 micrometers to 2 millimeters in height.

The fluid can include liquids having low ultrasonic attenuation (e.g., featuring energy loss less than 0.1 dB/cm around 1 MHz operation frequency). The fluid can be liquids such as, but not limited to, water, methanol, dielectric fluorocarbon fluid, organic solvent, other liquids having a low ultrasonic attenuation, and combinations thereof. The fluids can include one or more molecules that can be solvated and ionized. The molecules can include, but are not limited to, polynucleotides, polypeptides, and combinations thereof.

The actuator 42 produces a resonant ultrasonic wave 52 within the reservoir 32 and fluid. As mentioned above, the resonant ultrasonic wave 52 couples to and transmits through the liquid and is focused by the ejector structures 26 to form a pressure gradient 54 within the ejector structure 26. The high-pressure gradient 54 accelerates fluid out of the ejector structure 26 to produce droplets. The droplets are produced discretely in a drop-on-demand manner. The frequency in which the droplet are formed is a function of the drive cycle applied to the actuator 42 as well as the fluid, reservoir 32, ejector structure 26, and the ejector nozzle 24.

An alternating voltage is applied (not shown) to the actuator 42 to cause the actuator 42 to produce the resonant ultrasonic wave 52. The actuator 42 can operate at about 100 kHz to 100 MHz, 500 kHz to 15 MHz, and 800 kHz to 5 MHz. A direct current (DC) bias voltage can also be applied to the actuator 42 in addition to the alternating voltage. In embodiments where the actuator 42 is piezoelectric, this bias voltage can be used to prevent depolarization of the actuator 42 and also to generate an optimum ambient pressure in the reservoir 32. In embodiments where the actuator 42 is electrostatic, the bias voltage is needed for efficient and linear operation of the actuator 42. Operation of the actuator 42 is optimized within these frequency ranges in order to match the cavity resonances, and depends on the dimensions of and the materials used for fabrication of the reservoirs 32 and the array structure 22 as well the acoustic properties of the fluids inside ejector.

The actuator 42 can include, but is not limited to, a piezoelectric actuator and a capacitive actuator. The piezoelectric actuator and the capacitive actuator are described in X. C. Jin, I. Ladabaum, F. L. Degertekin, S. Calmes and B. T. Khuri-Yakub, "Fabrication and Characterization of Surface Micromachined Capacitive Ultrasonic Immersion Transducers", IEEE/ASME Journal of Microelectromechanical Systems, 8, pp. 100-114, 1999 and Meacham, J. M., Ejimofor, C., Kumar, S., Degertekin F. L., and Fedorov, A., A micromachined ultrasonic droplet generator based on liquid horn structure, Rev. Sci. Instrum., 75 (5), 1347-1352 (2004)., which are incorporated herein by reference.

The dimensions of the actuator 42 depend on the type of actuator used. For embodiments where the actuator 42 is a piezoelectric actuator, the thickness of the actuator 42 is determined, at least in part, by the frequency of operation and the type of the piezoelectric material. The thickness of the piezoelectric actuator is chosen such that the thickness of the actuator 42 is about half the wavelength of longitudinal waves in the piezoelectric material at the frequency of operation. Therefore, in case of a piezoelectric actuator, the dimensions of the actuator 42 are from 100 micrometers to 4 centimeters in width, 10 micrometers to 1 centimeter in thickness, and 100 micrometers to 4 centimeters in length. In addition, the dimensions of the actuator 42 are from 100 micrometers to 2 centimeters in width, 10 micrometers to 5 millimeters in thickness, and 100 micrometers to 2 centimeters in length. Further, the dimensions of the actuator 42 are from 100 micrometers to 1 centimeters in width, 10 micrometers to 2 millimeters in thickness, and 100 micrometers to 1 centimeters in length.

In embodiments where the actuator 42 is an electrostatic actuator, the actuator 42 is built on a wafer made of silicon, glass, quartz, or other substrates suitable for microfabrication, where these substrates determine the thickness of the actuator 42. Therefore, in case of a microfabricated electrostatic actuator, the dimensions of the actuator 42 are from 100 micrometers to 4 centimeters in width, 10 micrometers to 2 millimeter in thickness, and 100 micrometers to 4 centimeters in length. In addition, the dimensions of the actuator 42 are from 100 micrometers to 2 centimeters in width, 10 micrometers to 1 millimeter in thickness, and 100 micrometers to 2 centimeters in length. Further, the dimensions of the actuator 42 are from 100 micrometers to 1 centimeters in width, 10 micrometers to 600 micrometers in thickness, and 100 micrometers to 1 centimeter in length.

In the embodiment illustrated in FIG. 2, the ionization source 44 is disposed on the surface of the actuator 42 adjacent the reservoir 32. A direct current bias voltage can be applied to the ionization source 44 via one or more sources through line 46. The voltage applied to the ionization source 44 is substantially lower than that applied in currently used electrospray systems. The voltage applied to the ionization source 44 should be sufficient enough to cause charge separation to ionize the molecules present in the fluid. In this regard, the voltage applied to the ionization source 44 should be capable to produce redox reactions within the fluid. Therefore, the voltage applied to the ionization source 44 will depend, at least in part, upon the fluid and molecules present in the fluid. The voltage applied to the ionization source depends, in part, on the electrochemical redox potential of the given sample analyte and is typically from about 0 to 1000V, 20 to 600V, and 80 to 300V.

The ionization source 44 can include, but is not limited to, a wire electrode, a conductive material disposed on the reservoir 32, and an electrode of the actuator 42, and combinations thereof. The material that the wire and/or the conductive material is made of can include, but is not limited to, metal (e.g., copper, gold, and/or platinum), conductive polymers, and combinations thereof. The ionization source 44 may cover a small fraction (1%) or an entire surface (100%) of the actuator 42. The ionization source 44 has a thickness of about 1 nanometer to 100 micrometers, 10 nanometers to 10 micrometers, and 100 nanometers to 1 micrometer.

Figure 3:
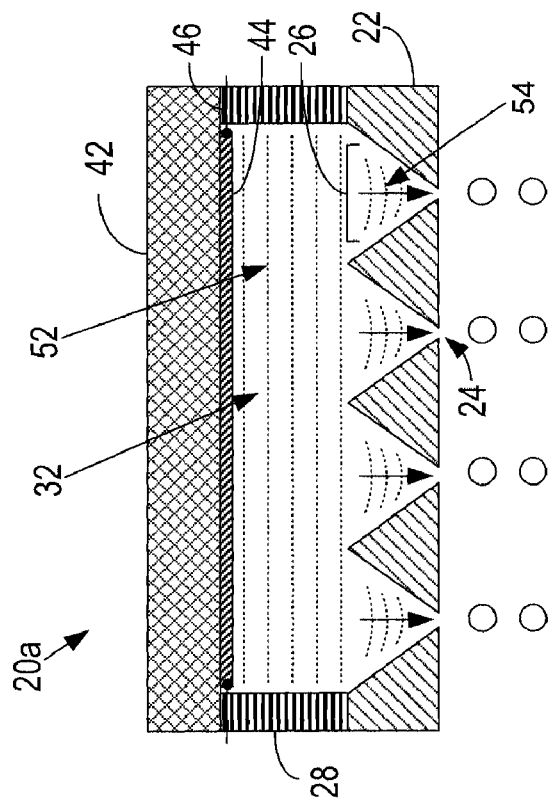
FIG. 3 is an illustration of a cross-section of another embodiment of an electrospray system, as shown in FIG. 1.

FIG. 3 is an illustration of a cross-section of another embodiment of an electrospray system 20b, as shown in FIG. 1. In this embodiment, a second ionization source 62 is disposed on portions of the inside surfaces of ejector structures 26. An electrical potential can be applied to the second ionization source 62 via one or more sources through a line 64. As in the embodiment shown in FIG. 2, the second ionization source 62 can be made of similar materials and dimensions. The second ionization source 62 can cover a small fraction (about 1% or just a tip) or an entire surface (100%) of the nozzle inner surface. This ionization source may not only produce ionization of molecules in the fluid when operated in DC mode, but also can support formation of electrocapillary waves at the fluid interface near the nozzle tip when operated in the AC mode in order to facilitate formation the droplets whose size is even smaller than the nozzle tip opening.

The following fabrication process is not intended to be an exhaustive list that includes all steps required for fabricating the electrospray system 20b. In addition, the fabrication process is flexible because the process steps may be performed in a different order than the order illustrated in FIGS. 4A through 4J.

Figure 4I:
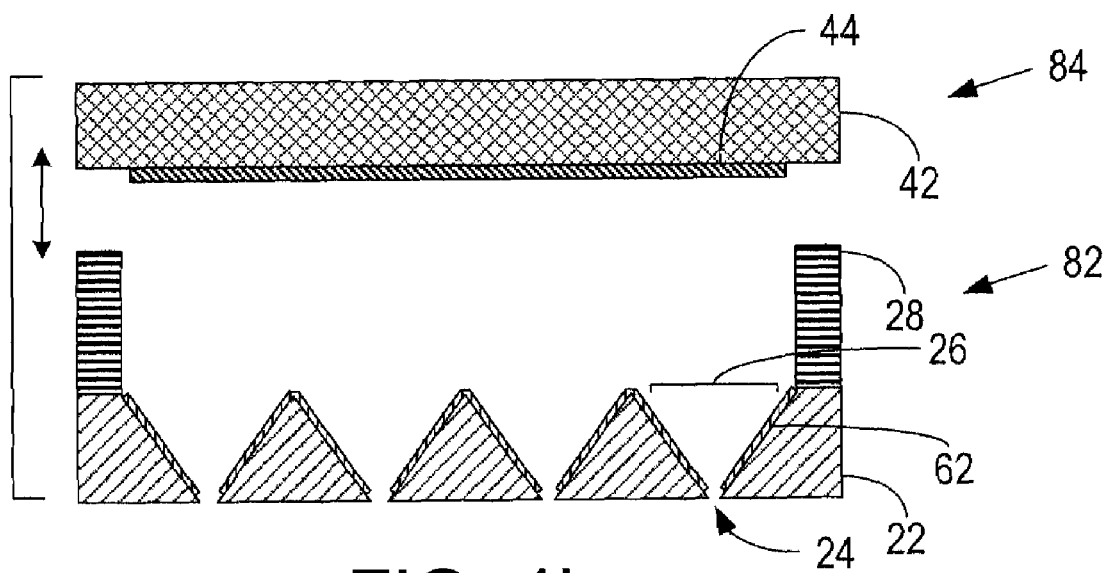

FIGS. 4A through 4J are illustrations of cross-sections of a representative embodiment of a method of forming the electrospray system shown in FIG. 3. FIG. 4A illustrates an array substrate 72 having a first masking layer 74 disposed thereon and patterned using photolithographic techniques. The first masking layer 74 can be formed of materials such as, but not limited to, a silicon nitride mask (Si3N4). The first mask layer 74 can be formed using techniques such as, but not limited to, plasma enhanced chemical vapor deposition, low pressure chemical vapor deposition, and combinations thereof. The patterning of the first masking layer 74 is done using standard photolithography techniques.

FIG. 4B illustrates the array substrate 72 after being etched to form the array structure 22 having ejector structures 26 formed in areas where the mask 74 was not disposed. The etching of the array substrate 72 to form the ejector structures 26. The etching technique can include, but is not limited to, a potassium hydroxide (KOH) anisotropic etch, reactive ion etching (RIE), and inductively coupled plasma etch (ICP), and focused ion beam (FIB) machining. It should also be noted that the array substrate 72 can be formed via stamping, molding, or other manufacturing technique.

An example of etching includes, but is not limited to, the formation of a pyramidal ejector structure having internal wall angles of about 54.74° using anisotropic KOH etch of a single crystal silicon wafer from the (100) surface. The KOH solution etches the exposed (100) planes more rapidly than the (111) planes to form the pyramidal ejector structure such as described in Madou, M. J. (2002). Fundamentals of Microfabrication. Boca Raton, Fla., CRC Press.

FIG. 4C illustrates the removal of the first masking layer 74 using a reactive ion etching (RIE) process or similar process, if necessary, while FIG. 4D illustrates the addition of a second masking 76. The second masking layer 76 can be formed of materials such as, but not limited to, a photoresist mask, a silicon nitride (hard) mask (Si3N4), and a silicon oxide (hard) mask (SiO2) which is patterned using photolithography techniques. The second masking layer 76 can be formed using techniques such as, but not limited to photolithography etching, inductively coupled plasma (ICP) etching, and reactive ion etching (RIE), and combinations thereof.

FIG. 4E illustrates the etching of the second mask layer 76 to form the ejector nozzle 24 in the array substrate 22. The etching technique can include, but is not limited to, photolithography etching, inductively coupled plasma (ICP) etching, and reactive ion etching (RIE). Alternatively, depending on the size and geometry, the ejector nozzles 24a and 24b can be cut from the wafer, using a dicing saw or other similar device. Also, the ejector nozzles 24a and 24b can be machined using focused ion beam (FIB), and laser or electron beam (E-beam) drilling as opposed to using the second mask layer 76.

FIG. 4F illustrates the removal of the second mask layer 76 using a reactive ion etching (RIE) process or similar process. FIG. 4G illustrates the deposition of the second ionization source 62 on the inside wall of the ejector structure 26. The deposition techniques can include, but is not limited to, evaporation, sputtering, chemical vapor deposition (CVD), and electroplating.

FIG. 4H illustrates the placement of the separating layer 28 on portions of the array structure 22 to form the lower portion 82 of the electrospray system 20b. The separating layer 28 can be made separately by etching silicon, machining of the metal, or stamping the polymer. Once fabricated, this separating layer 28 can be bonded to the array structure 22 using a polyimide layer (such as Kapton™ or other bonding material). This dry film can be laminated and patterned using laser micromachining or photolithography techniques. The separating layer 28 can then be affixed/bonded to the piezoelectric transducer to form the operational device. Alternatively, the separating layer 28 is bonded to the upper portion 84 using a polyimide layer, for example. Then the separating layer 28 is bonded to the array structure 22.

Figure 4J:
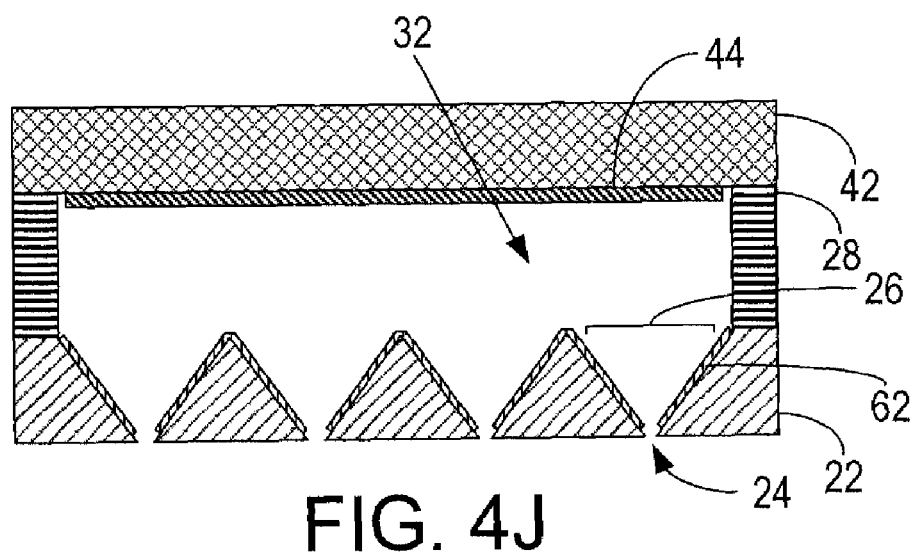

FIG. 4I illustrates the lower portion 82 of the electrospray system 20b and the upper portion 84 of the electrospray system 20b, while FIG. 4J illustrates the formation of the electrospray system 20b by joining (e.g., bonding and/or adhering) the lower portion 82 and the upper portion 84. It should be noted that the lower portion 82 could be produced separately and be used as a disposable cartridge that is replaced regularly on the electrospray system 20b, while the upper portion 84 is reused. In another embodiment not shown, the lower portion 82 does not include the separating layer 28 and the separating layer 28 is disposed on the upper portion 84, so that the upper portion 84 with the separating layer 28 disposed thereon is reused. In still another embodiment, the separating layer 28 can be removed separately from either the upper portion 84 and the lower portion 82.

FIG. 5 is an illustration of a cross-section of another embodiment of an electrospray system 12, as shown in FIG. 1. In this embodiment, the electrospray system 100 includes a first reservoir 32a and a second reservoir 32b. In addition, the first reservoir 32a and the second reservoir 32b each are adjacent a first actuator 42a and a second actuator 42b, respectively. Furthermore, the first reservoir 32a and the second reservoir 32b each are adjacent a first ejector structure 24a and a second ejector structure 24b, respectively.

The first reservoir 32a and the second reservoir 32b are separated by a center separating layer 28c. The first reservoir 32a is bound by the first separating layer 28a, the center separating layer 28c, the first actuator 42a, and the first ejector structure 26a. The second reservoir 32b is bound by the second separating layer 28b, the center separating layer 28c, the second actuator 42b, and the second ejector structure 26b. The same or a different fluid can be disposed in the first reservoir 32a and the second reservoir 32b, chosen to match the acoustic properties of the sample loaded in the cavity of the ejector structures 26a and 26b, respectively. This configuration allows one to generate electrosprays of different fluids by simply electronically choosing the first actuator 42a, or the second actuator 42b. The number of the reservoirs can be increased by replicating this structure in the lateral dimension.

FIG. 6 is an illustration of a cross-section of another embodiment of an electrospray system 12, as shown in FIG. 1. Similar to the electrospray system 100 shown in FIG. 5, the electrospray system 120 shown in FIG. 6 includes a first reservoir 32a and a second reservoir 32b. The first reservoir 32a is bound by the first separating layer 28a, the center separating layer 28c, the first actuator 42a, and the first ejector structure 22a. The first reservoir 32a includes a gas bubble (not shown). The second reservoir 32b is bound by the second separating layer 28b, the center separating layer 32c, a second actuator 42b, and the second ejector structure 22b. The second reservoir 32b includes a fluid bubble 208.

Figure 7:
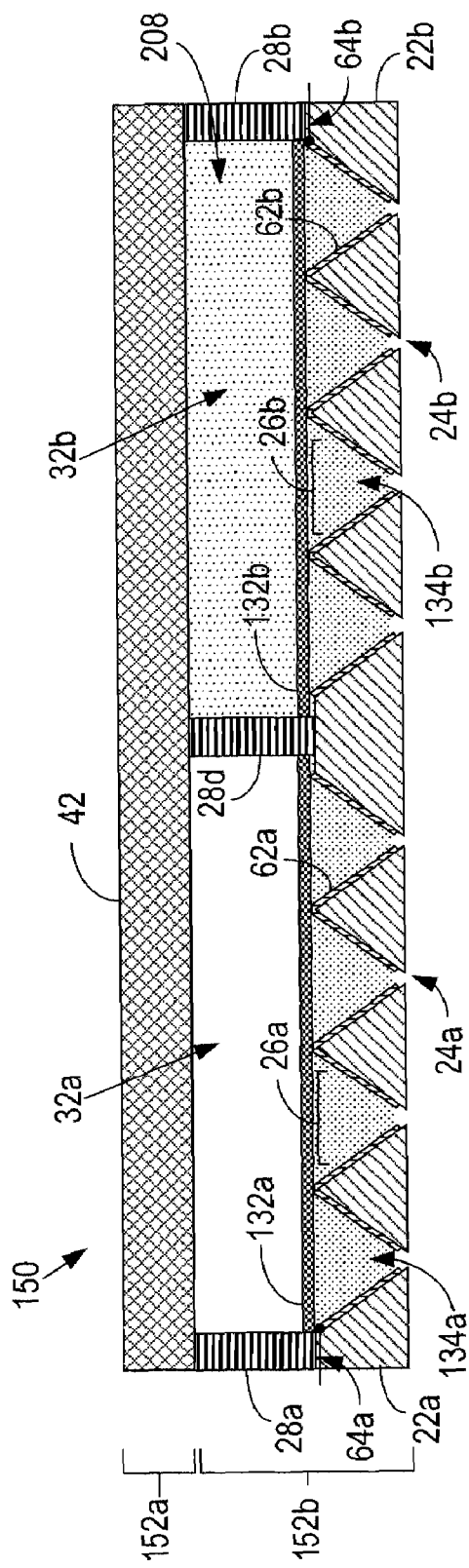
FIG. 7 is an illustration of a cross-section of another embodiment of an electrospray system, as shown in FIG. 1.

In addition, as shown in FIG. 7, the electrospray system 120 includes a first separating structure 132a and a second separating structure 132b, each disposed on top of the first ejection structure 26a and the second ejection structure 26b, respectively, separating the first reservoir 32a and the second reservoir 32b from the first array structure 22a and second array structure 22b, respectively. As demonstrated later with respect to FIGS. 8A through 8K, the first array structure 22a and second array structure 22b are filled with a first fluid 134a and a second fluid 134b, respectively, and then the first separating structure 132a and the second separating structure 132b are disposed on top of the first ejection structure 26a and the second ejection structure 26b. It should be noted that the electrospary system 120 does not include a first ionization source 44a and 44b since the first actuator 42a and the second actuator 42b are separated from the first fluid 134a and the second fluid 134b. This allows for individually addressable ionization sources, whose potential can be individually controlled.

The first separating structure 132a and the second separating structure 132b can be one structure or two distinct structures, which show little impedance to propagation of acoustic waves at the operation frequency of the actuators 42a and 42b. The first separating structure 132a and the second separating structure 132b can be made of materials such as, but not limited to polyimide layer (such as Kapton™), pyrolene, and other suitable materials. The first separating structure 132a and the second separating structure 132b can have a thickness of about 1 micrometers to 200 micrometers. The length and width of the first separating structure 132a and the second separating structure 132b will depend upon the dimensions of the first array structure 22a and second array structure 22b.

The first fluid 134a can be ejected out of the first ejection structure 26a by controllably positioning the fluid bubble (not shown) substantially between the first separating structure 132a and the first actuator 42a to fill in the reservoir 32a. Likewise, the second fluid 134b can be ejected out of the second ejection structure 26b by controllably positioning the fluid bubble 208 substantially between the second separating structure 132b and the second actuator 42b to fill in the reservoir 32b.

The ejection of the first fluid 134a and second fluid 134b can be controlled in at least two ways for the electrospray system 120 shown in FIG. 6. First, the first actuator 42a and the second actuator 42b can be individually activated to cause ejection of the first fluid 134a and the second fluid 134b if the fluid bubble 208 is properly positioned. Second, a gas bubble (not shown) can be positioned substantially between the first separating structure 132a and the first actuator 42a and/or the second separating structure 132b and the second actuator 42b. Since the gas bubble does not effectively couple to and transmit the ultrasonic pressure wave, the first fluid 134a and the second fluid 134b will not be ejected, even if the first actuator 42a and/or the second actuator 42b are activated. The process for selectively ejecting fluid from one or more ejector structures is described in further detail in FIGS. 9A though 9D and 10A through 10F.

FIG. 7 is an illustration of a cross-section of another embodiment of an electrospray system 12, as shown in FIG. 1. In contrast to the electrospray system 120 in FIG. 6, the electrospray system 150 shown in FIG. 7 includes only a single actuator 42 in communication with the first reservoir 32a and the second reservoir 32b. As in the electrospray system 120 in FIG. 6, the first fluid 134a can be ejected out of the first ejection structure 26a by controllably positioning the fluid bubble (not shown) substantially between the first separating structure 132a and the first actuator 42a to fill in the reservoir 32a. Likewise, the second fluid 134b can be ejected out of the second ejection structure 26b by controllably positioning the fluid bubble 208 substantially between the second separating structure 132b and the second actuator 42b to fill in the reservoir 32b.

In addition, the first fluid 134a can not be ejected out of the first ejection structure 26a when the gas bubble (not shown) is positioned substantially between the first separating structure 132a and the first actuator 42a to fill in the reservoir 32a. Likewise, the second fluid 134b can not be ejected out of the second ejection structure 26b when the gas bubble (not shown) is positioned substantially between the second separating structure 132b and the second actuator 42b to fill in the reservoir 32b.

Therefore, upon actuation of the actuator 42 and positioning of the fluid bubble 208 and the gas bubble, the ejection of the first fluid 134a and the second fluid 134b can be selectively controlled. For example, in the configuration in FIG. 7, actuation of the actuator 42 causes the second fluid 134b to be ejected, while the first fluid 134a is not ejected. The process for selectively ejecting fluid from one or more ejector structures is described in further detail in FIGS. 9A though 9C and 10A through 10E.

The following fabrication process is not intended to be an exhaustive list that includes all steps required for fabricating the electrospray system 150. In addition, the fabrication process is flexible because the process steps may be performed in a different order than the order illustrated in FIGS. 8A through 8K.

Figure 8A:
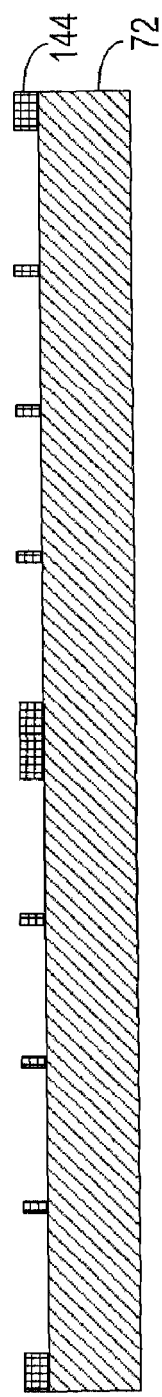

FIGS. 8A through 8K are illustrations of cross-sections of a representative embodiment of a method of forming the electrospray system shown in FIG. 7. FIG. 8A illustrates an array substrate 72 having a first masking layer 144 disposed thereon. The first masking layer 144 can be formed of materials such as, but not limited to, a silicon nitride mask (Si3N4), silicon oxide (SiO2) and patterned using standard photolithography techniques. The first mask 144 can be disposed using techniques such as, but not limited to, inductively coupled plasma (ICP) etch, reactive ion etch (RIE), or wet etching.

Figure 8B:
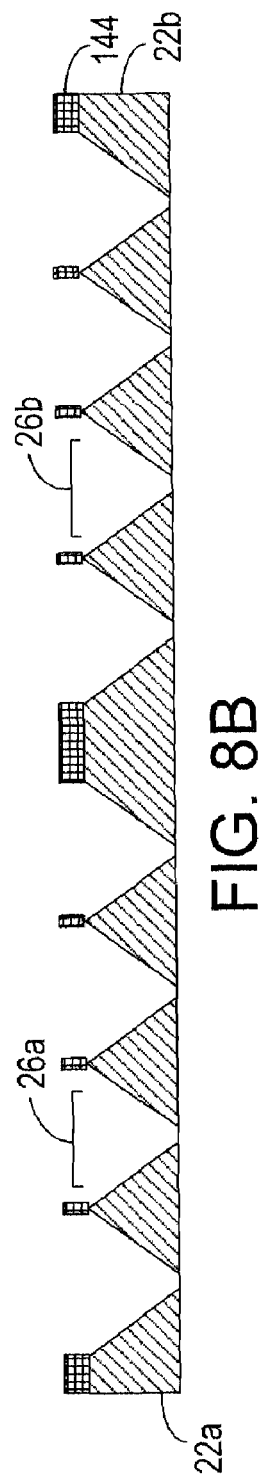

FIG. 8B illustrates the array substrate 72 after being etched to form the first array structure 22a and the second array structure 22b having the first ejector structures 26a and the second ejector structure 26b formed in areas where the mask 144 was not disposed. The etching of the array substrate 72 to form the first ejector structures 26a and the second ejector structure 26b). The etching technique can include, but is not limited to, a potassium hydroxide (KOH) anisotropic etch of (100) single crystal silicon and laser micro-machining.

Figure 8C:
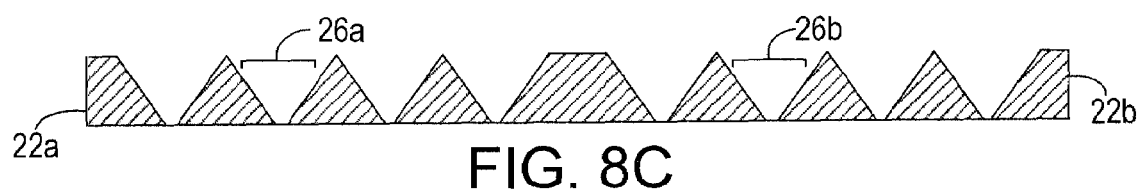
Figure 8D:

FIG. 8C illustrates the removal of the first mask 144 using a reactive ion etching (RIE) process or similar process, and FIG. 8D illustrates the addition of a second masking layer 152. The second mask 152 can be formed of materials such as, but not limited to, a silicon nitride mask (Si3N4), a silicon oxide mask (SiO2), or a photoresist.

Figure 8E:
Figure 8F:

FIG. 8E illustrates the etching of the second mask 152 to form the ejector nozzles 24a and 24b for the first ejector structure 26a and the second ejector structure 26b, respectively. The etching technique can include, but is not limited to, photolithography etching, inductively coupled plasma (ICP) etching, reactive ion etching (RIE), and wet chemical etching. Alternatively, depending on the size and geometry, the ejector nozzles 24a and 24b may be cut from the wafer, using a dicing saw or other similar device, and can be machined using focused ion beam (FIB), and laser or electron beam (E-beam) drilling, as opposed to using the second mask 152. FIG. 8F illustrates the removal of the second mask 152 using a reactive ion etching (RIE) process or similar process.

Figure 8G:
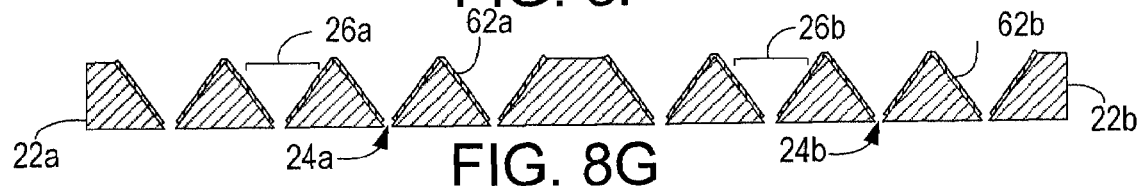

FIG. 8G illustrates the deposition of the second ionization source 62a and 62b on the inside wall of the first ejector structure 26a and the second ejector structure 26b, respectively. The deposition techniques can include, but are not limited to, evaporation, sputtering, chemical vapor deposition, and electroplating.

FIG. 8H illustrates the formation of the first separating structure 132a and the second separating structure 132b (these structures can be the same or be two distinct structures). In addition, an ejector nozzle sealing structure 136 is disposed on top of the ejector nozzles 24a and 24b of the first ejector structure 26a and second ejector structure 26b. The ejector nozzle sealing structure 136 can be made of materials such as, but not limited to, polyimide layer (such as Kapton) or some other inert layer such as parylene film.

Prior to the formation of the first separating structure 132a and the second separating structure 132b, the first ejector structure 26a and second ejector structure 26b are filled with a first fluid 134a and a second fluid 134b. The first fluid 134a and the second fluid 134b can be the same fluid or different fluids.

FIG. 8I illustrates the placement of the first separating layer 28a, the second separating layer 28b, and a center separating layer 28d on portions of the first array structure 22a and the second array structure 22b to form the lower portion 152 of the electrospray system 150. The first separating layer 28a, the second separating layer 28b, and a center separating layer 28d can each be made separately by etching silicon or simple machining of the metal or stamping the polymer. Once fabricated, the first separating layer 28a, the second separating layer 28b, and a center separating layer 28d each can be bonded to the nozzle array using a polyimide layer (such as Kapton). This dry film can be laminated and patterned using laser micro-machining or photolithography techniques. This spacer layer can then be affixed/bonded to the piezoelectric transducer to form the operational device.

It should be noted that the first separating layer 28a, the second separating layer 28b, and a center separating layer 28d can be disposed on portions of the first array structure 22a and the second array structure 22b prior to the formation of the first separating structure 132a and the second separating structure 132b and/or the ejector nozzle sealing structure 136. In addition, the first fluid 134a and the second fluid 134b can be disposed in the first ejector structure 26a and second ejector structure 26b after the first separating layer 28a, the second separating layer 28b, and the center separating layer 28d are formed.

In this regard, a structure including the first ejector structure 26a and the second ejector structure 26b and the first separating layer 28a, the second separating layer 28b, and the center separating layer 28d can be produced. Then in a separate process, the ejector nozzle sealing structure 136 can be positioned adjacent the first ejector nozzle 24a and the second ejector nozzle 24b, respectively. Subsequently, the first fluid 134a and the second fluid 134b can be dispensed into the first ejector structure 26a and second ejector structure 26b, respectively. Lastly, the first separating structure 132a and the second separating structure 132b can be disposed on the top of the first ejector nozzle 24a and the second ejector nozzle 24b, respectively.

In another embodiment not shown, the lower portion 152 does not include the first separating layer 28a, the second separating layer 28b, and the center separating layer 28d. The first separating layer 28a, the second separating layer 28b, and the center separating layer 28d are disposed on the upper portion 154. Therefore, the upper portion 154 with the first separating layer 28a, the second separating layer 28b, and the center separating layer 28d disposed thereon can be reused. In still another embodiment, the first separating layer 28a, the second separating layer 28b, and the center separating layer 28d can be removed separately from either the upper portion 154 or the lower portion 152.

FIG. 8J illustrates the lower portion 152 of the electrospray system 150 and the upper portion 154 of the electrospray system 150, and FIG. 8K illustrates the formation of the electrospray system 150 by joining (e.g., bonding and/or adhering) the lower portion 152 and the upper portion 154. It should be noted that the lower portion 152 could be produced separately and be used as a disposable cartridge that is replaced regularly on the electrospray system 150, while the upper portion 154 is reused.

FIGS. 9A through 9D are illustrations of top views of representative embodiments of an electrospray system 200. FIG. 9B illustrates a fluid bubble in one section of the electrospray system 200, while FIG. 9C illustrates a fluid bubble in the other section of the electrospray system 200. The electrospray system 200 has a single actuator (not shown) positioned in communication with a first reservoir 202a and a second reservoir 202b. The first reservoir 202a and the second reservoir 202b are separated from each other by a separating layer 206. The first reservoir 202a and the second reservoir 202b are separated from the array structure (not shown) having a first ejector structure 204a and a second ejector structure 204b by a first separating structure and a second separating structure (not shown). The first ejector structure 204a and the second ejector structure 204b each contain a fluid within their respective cavities.

FIG. 9A illustrates the electrospray system 200 in a state where only gas bubbles (not shown) are positioned within the first reservoir 202a and the second reservoir 202b. As mentioned above, a gas bubble does not effectively couple to and transmit the ultrasonic pressure wave, so upon actuation of the actuator substantially no fluid is ejected from the first ejector structure 204a and the second ejector structure 204b.

FIG. 9B illustrates an acoustically responsive fluid bubble 208 in the second reservoir 202b of the electrospray system 200. Since the fluid bubble 208 can substantially couple to and transmit the ultrasonic pressure wave, actuation of the actuator causes the fluid within the second ejector structure 204b to be ejected through the ejectors nozzles of the second ejector structure 204b, but substantially no fluid is ejected from the first ejector structure 204a since the gas bubble does not effectively couple to and transmit the ultrasonic pressure wave produced by the actuator.

FIG. 9C illustrates an acoustically responsive fluid bubble 208 in the first reservoir 202a of the electrospray system 200. Since the fluid bubble 208 can substantially couple to and transmit the ultrasonic pressure wave, actuation of the actuator causes the fluid within the first ejector structure 204a to be ejected through the ejectors nozzles of the first ejector structure 204a, but substantially no fluid is ejected from the second ejector structure 204b since the gas bubble does not effectively couple to and transmit the ultrasonic pressure wave produced by the actuator.

FIG. 9D illustrates acoustically responsive fluid bubbles 208 in the first reservoir 202a and the second reservoir 202b of the electrospray system 200. Since the fluid bubble 208 can substantially couple to and transmit the ultrasonic pressure wave, actuation of the actuator causes the fluid within the first ejector structure 204a and the second ejector structure 204b to be ejected through the ejectors nozzles of the first ejector structure 204a and the second ejector structure 204b.

FIGS. 10A through 10F are illustrations of top views of representative embodiments of an electrospray system 220 that may be used in a multiplexing format and/or parallel analysis. FIGS. 10B through 10E illustrate an acoustically responsive fluid bubble 208 being positioned from one section of the electrospray system 220 to another. The electrospray system 220 has a single actuator (not shown) positioned in communication with a first reservoir 222a, a second reservoir 222b, a third reservoir 222c, and a fourth reservoir 222d. The first reservoir 222a, the second reservoir 222b, the third reservoir 222c, and the fourth reservoir 222d are separated from each other by a first separating layer 226a and a second separating layer 226b. The first reservoir 222a, the second reservoir 222b, the third reservoir 222c, and the fourth reservoir 222d are separated from the array structure (not shown) having a first ejector structure 224a, a second ejector structure 224b, a third ejector structure 224c, and a fourth ejector structure 224d, by a first separating structure, a second separating structure, a third separating structure, and a fourth separating structure (not shown). The first reservoir 222a, the second reservoir 222b, the third reservoir 222c, and the fourth reservoir 222d, each contain a fluid within their respective cavities.

FIG. 10A illustrates the electrospray system 220 in a state where only gas bubbles (not shown) are positioned within the first reservoir 222a, the second reservoir 222b, the third reservoir 222c, and the fourth reservoir 222d. As mentioned above, a gas bubble does not effectively couple to and transmit the ultrasonic pressure wave. Thus, upon actuation of the actuators substantially no fluid is ejected from the first ejector structure 224a, the second ejector structure 224b, the third ejector structure 224c, and the fourth ejector structure 224d.

Similar to FIGS. 9A through 9D, an acoustically responsive fluid bubble 208 is controllably moved from the first reservoir 222a to the fourth reservoir 224c in a stepwise manner in FIGS. 10B through 10E. Since the fluid bubble 208 can substantially couple to and transmit the ultrasonic pressure wave, actuation of the actuator causes the fluid within the ejector structure having the fluid bubble disposed in the corresponding reservoir to be ejected through the ejectors nozzles of the that ejector structure. However, substantially no fluid is ejected from the other ejector structures since the gas bubble does not effectively couple to and transmit the ultrasonic pressure wave produced by the actuator.

FIG. 10F illustrates an acoustically responsive fluid bubble 208 in the first reservoir 222a and the fourth reservoir 224c. Since the fluid bubble 208 can substantially couple to and transmit the ultrasonic pressure wave, actuation of the actuator causes the fluid within first ejector structure 224a and the fourth ejector structure 224d to be ejected through the ejectors nozzles of the each ejector structure. In other embodiments, the fluid bubble 208 can be positioned in one or more of the reservoirs so that one or more fluids within the ejector structures can be ejected simultaneously.

While embodiments of electrospray system are described in connection with Examples 1 and 2 and the corresponding text and figures, there is no intent to limit embodiments of the electrospray system to these descriptions. On the contrary, the intent is to cover all alternatives, modifications, and equivalents included within the spirit and scope of embodiments of the present disclosure.

EXAMPLE 1

Figure 11:
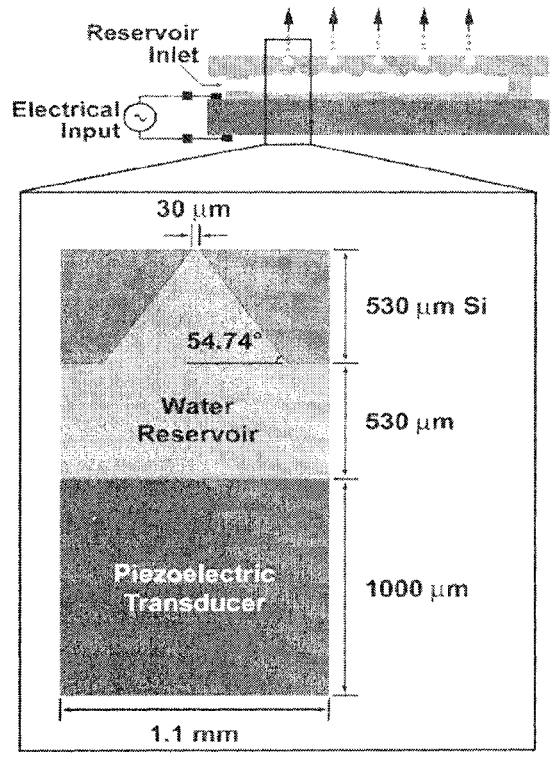
FIG. 11 is a schematic of a representative micro-machined ultrasonic droplet generator.

On-Demand Droplet Formation and Ejection using Micromachined Ultrasonic Atomizer While embodiments of electrospray system are described in connection with examples 1 and 2 and the corresponding text and figures, there is no intent to limit embodiments of the electrospray system to these descriptions. On the contrary, the intent is to cover all alternatives, modifications, and equivalents included within the spirit and scope of embodiments of the present disclosure. An exemplary embodiment of a representative electrospray system has been developed and tested on a mass spectrometer (MS). As shown in FIG. 11, it includes of a piezoelectric transducer, a fluid reservoir, and a silicon cover plate containing the micromachined ejector nozzles, similar to the design in FIG. 1. A PZT-8 ceramic is selected for the piezoelectric transducer. The device generates droplets by utilizing cavity resonances in the about 1 to 5 MHz range, along with the acoustic wave focusing properties of liquid horns formed by a silicon wet etching process. At resonance, a standing acoustic wave is formed in the fluid reservoir with the peak pressure gradient occurring at the tip of the nozzle leading to droplet ejection. Finite element analysis using ANSYS (2003) not only confirms the acoustic wave focusing by the horn structure shown in FIG. 11, but also accurately predicts the resonant frequencies at which the device provides stable droplet ejection.

Figure 12:
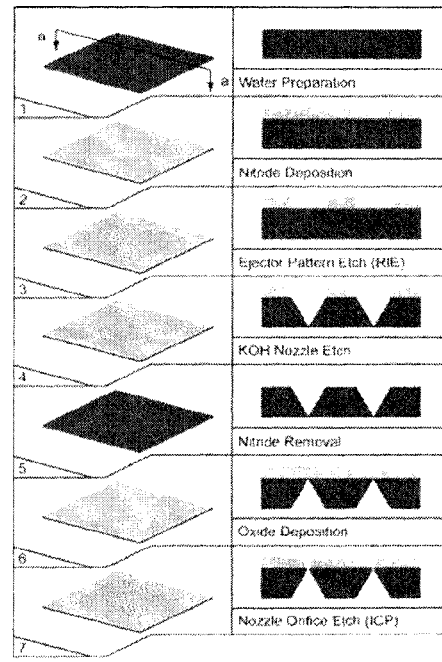
FIG. 12 is a schematic of a representative process for forming the micro-machined ultrasonic droplet generator illustrated in FIG. 11.

Although a number of horn shapes are capable of focusing acoustic waves, a pyramidal shape was selected as it can be readily fabricated via, for example, a single step potassium hydroxide (KOH) wet etch of (100) oriented silicon. As shown in FIG. 12, when square patterns are opened in a mask layer material, such as silicon nitride (FIG. 12, steps 2 and 3), deposited on the surface of a (100) oriented silicon wafer, and the edges are aligned to the <110> directions, the KOH solution etches the exposed (100) planes more rapidly than the (111) planes yielding a pyramid shaped horn (FIG. 12, step 4) making a 54.74° angle with the plane of the wafer. The sizes of the square features representing the base of the pyramid are designed so that the tip of these focusing pyramidal horns terminate within about 1 to 20 μm of the opposite surface of the ejector plate.

Figure 13A:
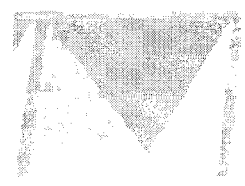
FIGS. 13A and 13B illustrate scanning electron micrographs (SEMs) of a KOH-etched pyramid-shaped horn with an ICP etched nozzle at the apex (FIG. 13A) and an array of nozzles fabricated on a silicon wafer (FIG. 13B).
Figure 13B:
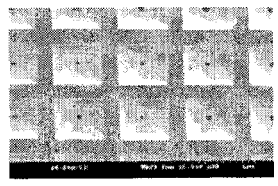

As the last step of the process, the nozzles of the desired diameter (about 3 to 5 μm in this embodiment) are formed by exemplary dry etching the remaining silicon from the opposite side in inductively coupled plasma (ICP) using a patterned silicon oxide layer as the hard mask (FIG. 12, steps 6 and 7). As shown in the Scanning Electron Micrographs (SEMs) in FIGS. 13A and 13B, this simple exemplary process, with only two masks and two etching steps, has been used to fabricate hundreds of pyramidal horns with nozzles on a single silicon wafer.

Figure 14A:
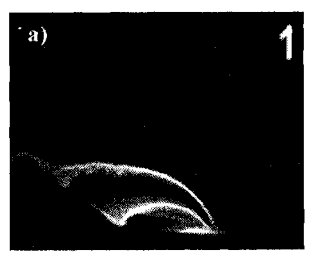
FIG. 14A illustrates a droplet ejection from several nozzles of a prototype device.
Figure 14B:
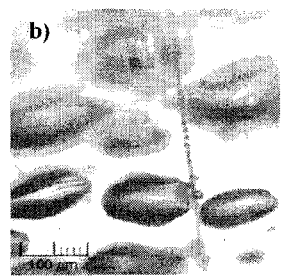
FIG. 14B illustrates a stroboscopic image of a jet of about 8 μm diameter droplets ejected by a representative electrospray system.
Figure 14C:
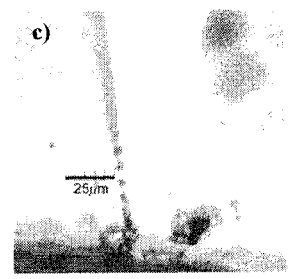
FIG. 14C illustrates a stroboscopic image of a jet of 5 μm droplets ejected by a representative electrospray system.

FIGS. 14A through 14C illustrate the device in operation, where the clouds of generated aerosol are emanating from the device. FIG. 14B and 14C show enhanced stroboscobic images of about 8 μm and about 5 μm diameter water droplets ejected from a single nozzle on different wafers, at a frequency of about 1.4 MHz and about 916 kHz, respectively. By making the nozzles even smaller or exploiting the instabilities of the liquid interface during droplet formation (e.g., by promotion formation of electrocapillary waves at the fluid interface), it may be possible to produce even smaller, sub-micron droplets using this droplet generation technology.

EXAMPLE 2

Electrospray Generation of Protein Ions at Low Applied Voltages and MS Analysis

Figure 15:
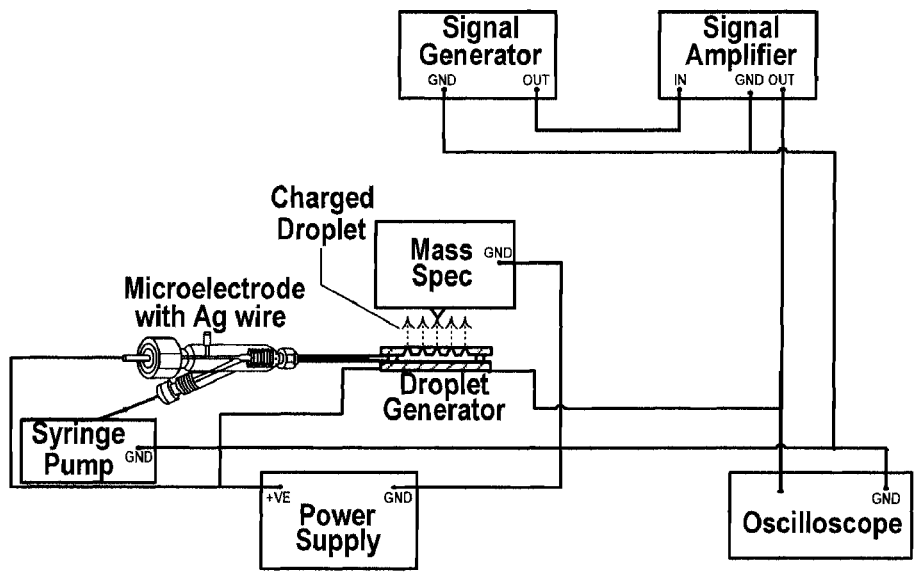
FIG. 15 illustrates a schematic of a representative experimental setup for experimental characterization of the micro-machined ultrasonic electrospray array when interfaced with a mass spectrometer (MS).
Figure 16:
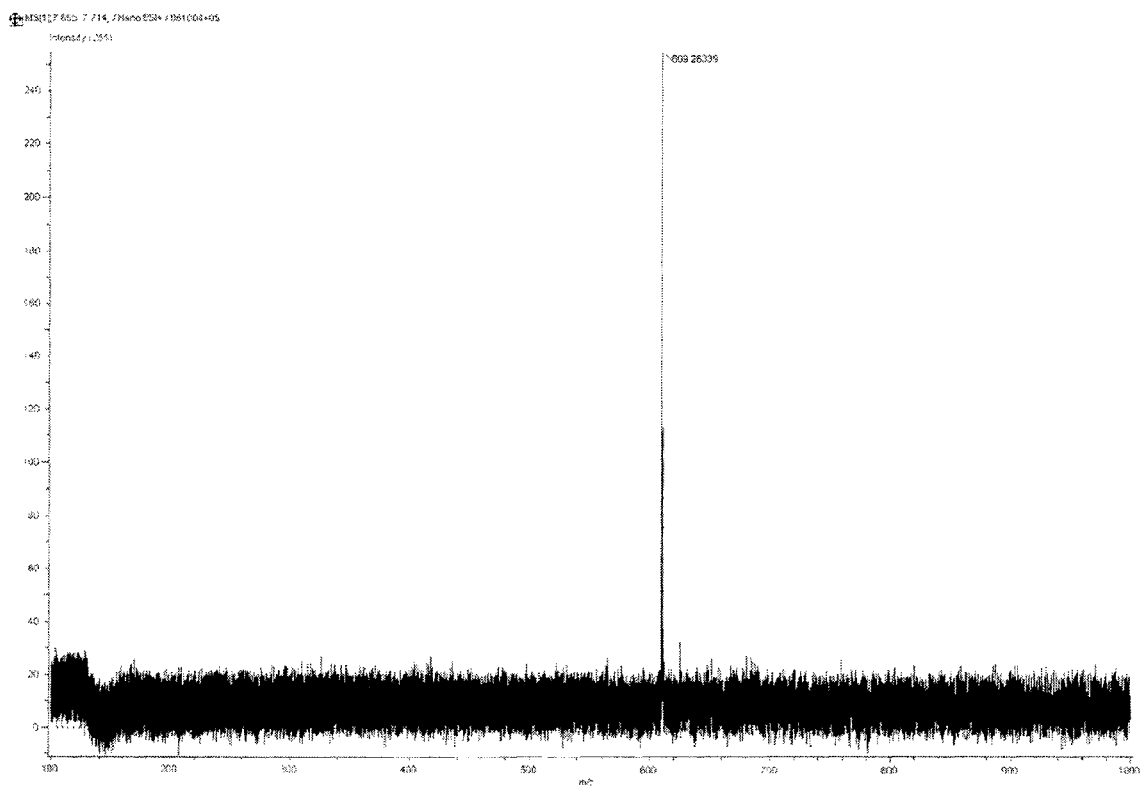
FIG. 16 illustrates an MS spectra of the MeOH:H20:Acetic Acid (50:49.9:0.1) solvent mixture containing a standard low molecular weight test compound reserpine (MW=609 Da, CAS# 50-55-5) ionized using the electrospray system.

Protein ions suitable for high sensitivity mass spectrometric analysis with an ionization voltage below 300 V (rather than kilovolts required by the conventional nanospray sources) have been produced using embodiments of the electrospray system. FIG. 15 illustrates a schematic of the experimental setup in which an electrode of the piezoelectric transducer is also used for electrochemical charging of the fluid by applying DC bias voltage in addition to the AC signal used for sound waves generation. FIG. 16 shows a strong peak of the 609 Da molecular weight compound (with signal-to-noise ratios of 3 or better) obtained in MS analysis of the mixture containing a standard low molecular weight test peptide, such as reserpine (MW=609 Da, CAS# 50-55-5), ionized using the embodiment of the electrospray system.

Figure 17A:
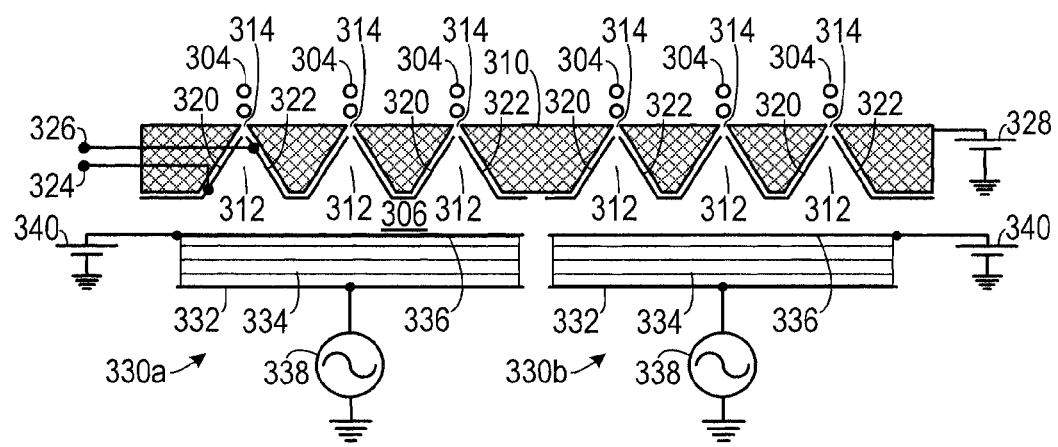
FIG. 17A is a cross-sectional view of one embodiment that may be employed cell manipulation.

One embodiment of the invention may be used in cellular manipulation, such as: lysis (disruption of a cell membrane and removal of material from the cell), poration (opening pores in a cell membrane to enable material transfer to and from the cell), transfection (moving material into cells through the cell membrane) and sorting. As shown in FIG. 17A, a cellular manipulation embodiment includes a substrate 310 (such as a silicon wafer) defining a plurality of tapering passages 312 (such as pyramidal or frusto-conical passages) that terminate in openings 314 passing through the substrate 310. Each tapering passage 312 includes a first poration electrode 320, electrically coupled to a first electrical contact 324, and a spaced-apart second poration electrode 322, electrically coupled to a second electrical contact 326 so that when a potential is applied between the first contact 324 and the second contact 326, an electric field will form between the first poration electrode 320 and the second poration electrode 322. A bias voltage 328 may also be applied to the substrate 310. Also, an oscillator may be used to drive the poration electrodes, thereby inducing an oscillating electric field.

An actuator 330a and 330b is spaced apart from the substrate 310 so as to form a cavity 306 therebetween. The actuator 330a and 330b are driven by an oscillator 338 to cause generation of an acoustic wave. If a fluid is placed in the cavity 306, then the acoustic wave will be focused by the tapering passages 312 onto the fluid. The spacing of the oscillator 338 from the substrate 310 and selection of the frequency of oscillation will determine the nature of the acoustic wave, and these variables may be tuned so as to generate a standing acoustic wave in the tapering passages 312. The acoustic wave may be focused by the passage 312 so that it has a predetermined compression geometry relative to the passage. Such a wave has a highly predictable pressure gradient that ensures that any cells placed in the tapering passages will be subject to a predetermined pressure at any given point along the tapering passage 312. Typically, the cells are suspended in a liquid placed into the cavity 306. The acoustic wave can then induce sonoporation of cells and can drive the cells through the openings 314 as ejected material 304. Thus, this embodiment may act as an electrostatic gun for transporting cellular material.

The actuator 330a and 330b, which can include an ultrasonic transducer, can include a layer of piezoelectric material 334 disposed between a first transducer electrode 332, which may be biased with a bias voltage 340, and an opposite second transducer electrode 336. The actuator 330a and 330b is oriented so that when a potential is applied between the first transducer electrode 332 and the second transducer electrode 336 (such as with the oscillator 338), the layer of piezoelectric material 334 expands or contracts, thereby generating an acoustic wave.

It is also possible to employ a capacitive transducer, that would include the first transducer electrode 332 and the second transducer electrode 336, but have only an air gap therebetween. When a potential is applied between the first transducer electrode 332 and the second transducer electrode 336, the second transducer electrode 336 moves relative to the first transducer electrode 332, thereby generating a wave.

When a potential is applied between the first poration electrode 320 and the second poration electrode 322, an electric field is generated. The electric field can cause electroporation of the cells. The combination of the electroporation and sonoporation can give rise to highly predictable poration of the cells. As the cell passes through the opening 314 the cell membrane allows the substance to pass therethrough. If a biologic material or a chemical composition (e.g., DNA, RNA, other genetic material, a pharmaceutical, a nano-particle, a dye, an imaging composition etc.) is placed in the liquid with the cells, then some of the material will pass into the cells as a result of the poration of the cells.

Likewise, if the electric field and acoustic wave have sufficient energy gradients, then highly predictable lysis can occur with the cells. This may be used to extract cellular material (e.g., DNA, RNA, genes, organelles, etc.) from the cells.

This embodiment may also be used in sorting cells by size. If the size of the openings 314 is such that only those cells smaller that a given size will pass through the openings, then the lager cells will stay behind.

Figure 17B:
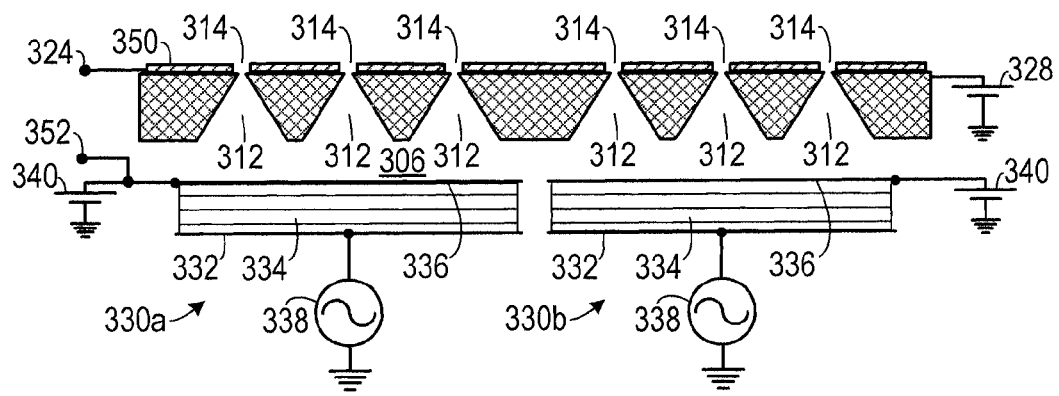
FIG. 17B is a cross-sectional view of a second embodiment that may be employed cell manipulation.

In the embodiment shown in FIG. 17B, first poration electrode may be co-incidental with the second transducer electrode 336 (and biased with voltage 352) and the second poration electrode 350 may be disposed adjacent to the second side of the substrate. Also, in one example, a dopant may also be added to the substrate 310 to allow it to act as a poration electrode.

Figure 18A:
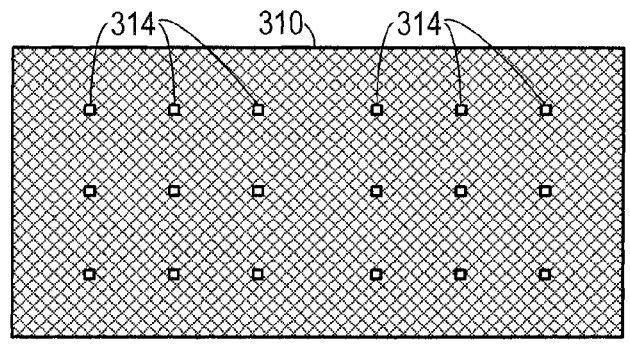
FIG. 18A is a plan view of an embodiment employing an array of tapering passages.
Figure 18B:
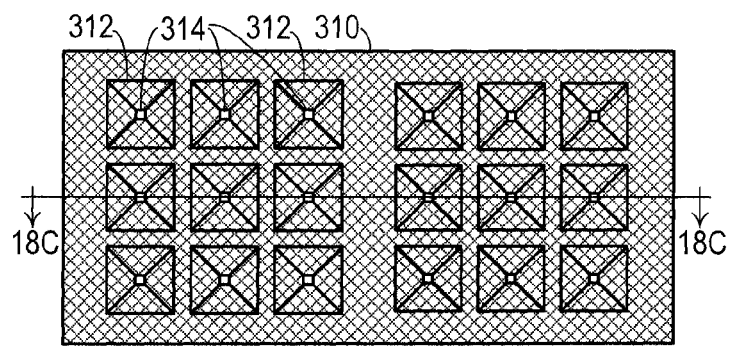
FIG. 18B is a plan view showing an opposite side of the embodiment shown in FIG. 18A.
Figure 18C:
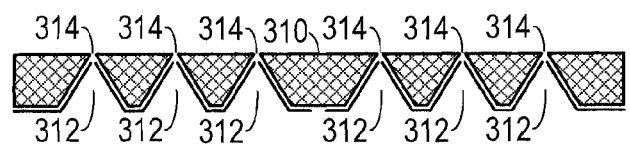
FIG. 18C is a cross-sectional view of the embodiment shown in FIG. 18B, taken along line 18C-18C.
Figure 19:
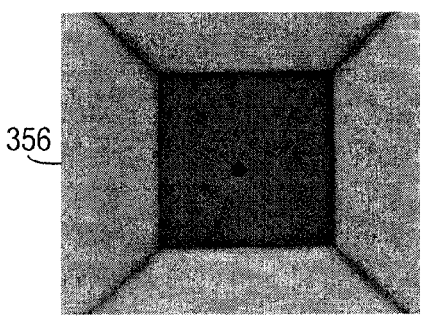
FIG. 19 is a micrograph of a tapering passage.

A plan view of one embodiment is shown in FIG. 18A, showing the substrate 310 and the openings 314. An opposite view is shown in FIG. 18B, showing the substrate 310, the tapering passages 312 and the openings 314. A cross section of this embodiment is shown in FIG. 18C. FIG. 19 shows a micrograph 356 of one of the tapering passages.

Figure 20A:
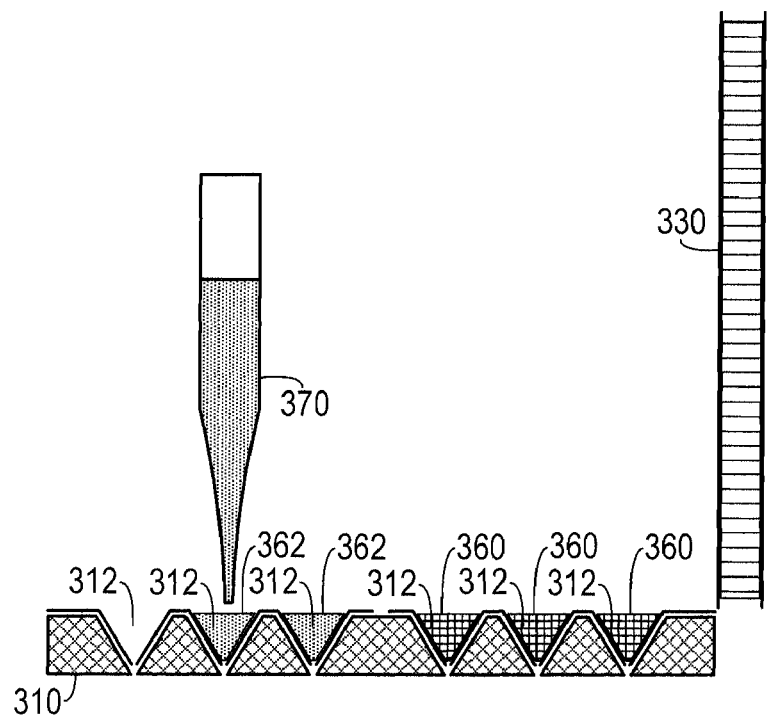
FIG. 20A is a schematic diagram showing the filling of tapering passages with differing materials.
Figure 20B:
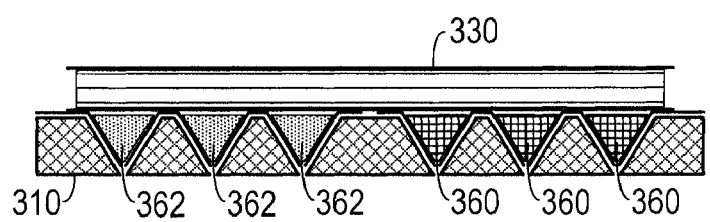
FIG. 20B is a schematic diagram showing the poration of the materials shown in FIG. 20A.

One embodiment, as shown in FIGS. 20A and 20B, may be used to process different analytes simultaneously. In this embodiment, the transducer 330 (which is shown as a unitary transducer in this example) may be detachable from the substrate 310 and the different analytes are placed into the passages 312 using a pipette 370. In the example shown a first analyte 360 is placed in several of the passages 312 and a second analyte 362 is placed in the remaining passages 312. The transducer 330 is replaced, as shown in FIG. 20B and operation continues as described above. In this example, the transducer 330 may be placed directly adjacent to the substrate 310, without an intervening cavity. In this example the first analyte 360 could include a first type of cell with the second analyte 362 could include a second type of cell. Also, different additives (such as different types of dye) may distinguish between the first analyte 360 and the second analyte 362. More than two different types of analyte may be analyzed simultaneously with this embodiment.

Figure 21:
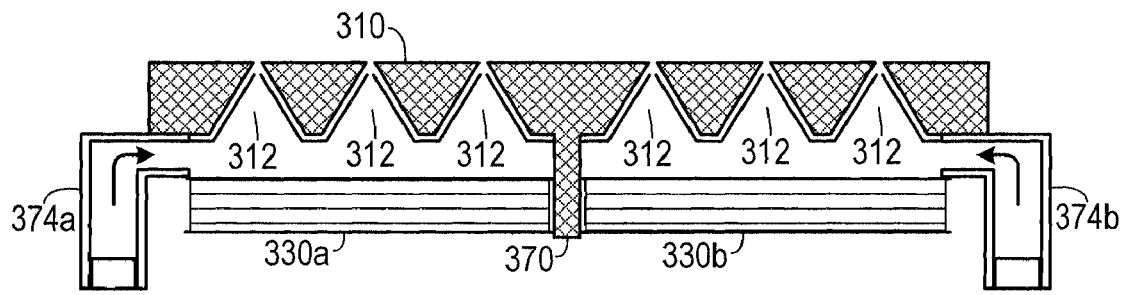
FIG. 21 is a cross-sectional view of an embodiment employing a fluid pump.

The invention may be used to manipulate cells continuously, as shown in FIG. 21, through use of a fluid pump 374a and 374b. In such an embodiment, as the cellular suspension is driven out of the passages 312, it is replaced by new fluid from the fluid pump 374a and 374b. Placing a wall 370 between a first portion of the passages and a second portion of the passages allows for analysis of different fluids (the first from a first fluid pump 374a and the second from a second fluid pump 374b) and with different energies (for example, using a first acoustic wave energy from the first acoustic transducer 330a and a second acoustic wave energy from the second acoustic transducer 330b).

Figure 22:
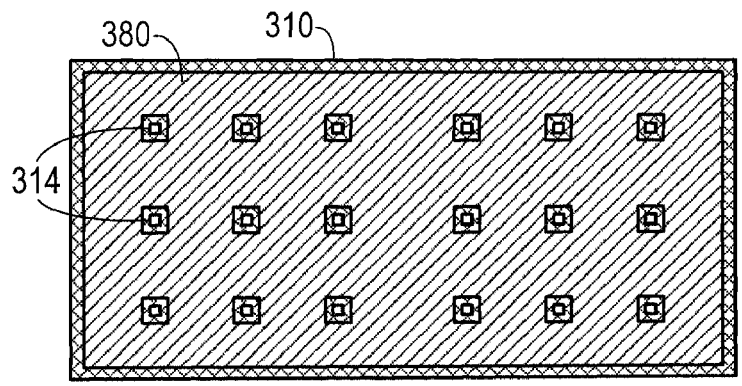
FIG. 22 is a plan view of an embodiment employing a planar poration electrode.
Figure 23:
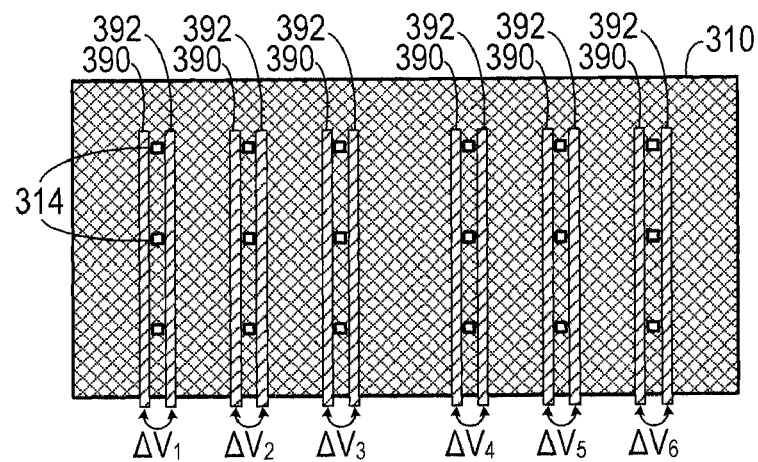
FIG. 23 is a plan view of an embodiment employing a plurality of independently addressable first poration electrode-second poration electrode pairs.

As shown in FIG. 22, the second poration electrode 380 might be disposed on the top surface of the substrate 310. Also, as shown in FIG. 23, the first poration electrode 390 may include a plurality of conductive strips placed on the substrate 310 along each row of openings 314. The second poration electrode 392 may also include a plurality of conductive strips placed on the substrate 310 along each row of openings 314. This way, each strip might be a separately addressable sub-electrode to allow for the application of a different potential (? V1-? V6) for each poration sub-electrode pair.

Figure 24A:
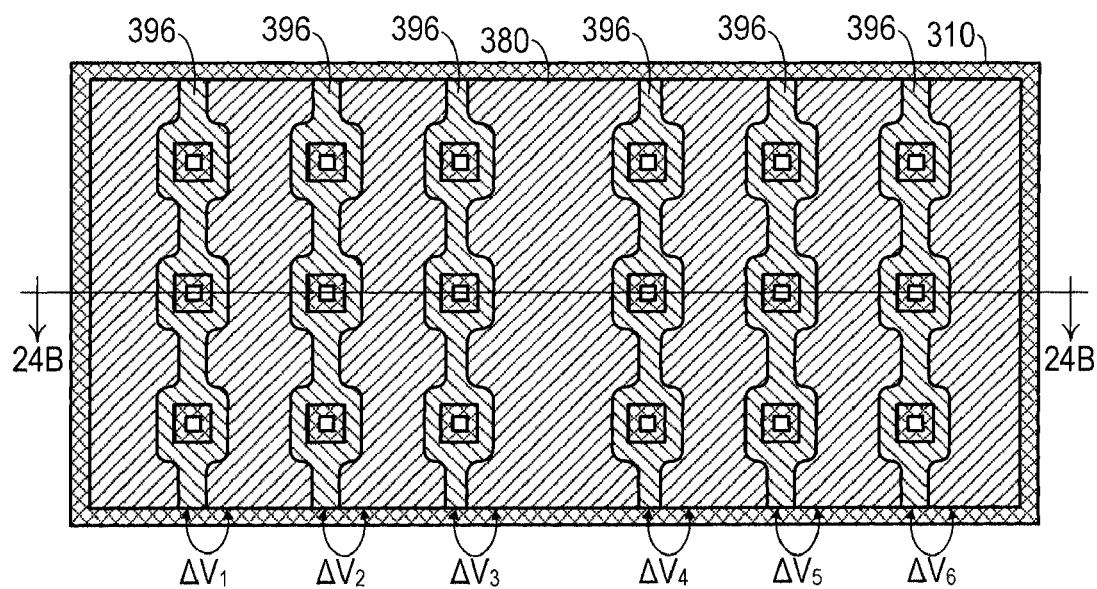
FIG. 24A is a plan view of an embodiment employing a planar second poration electrode and a plurality of independently addressable first poration electrodes.
Figure 24B:
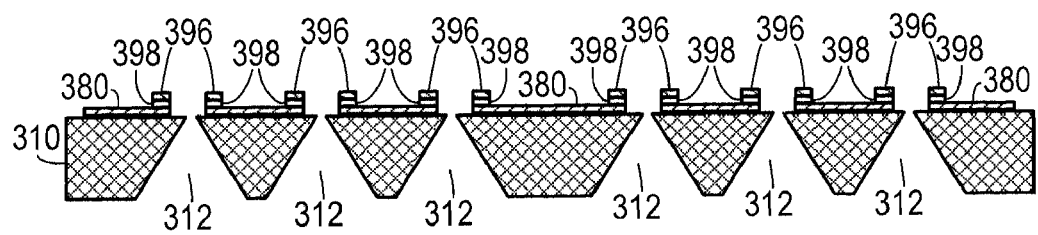
FIG. 24B is a cross-sectional view of the embodiment shown in FIG. 24A, taken along line 24B-24B.

Another way to accomplish the application of different electrical fields being applied to different passages 312 is shown in FIGS. 24A and 24B. In this embodiment, the second poration electrode 380 is applied to the substrate, a layer of an insulator layer 398 is applied onto the first poration electrode 380 and then a first poration electrode layer is applied to the insulator layer 398. The first poration electrode layer is patterned (e.g., through etching) to create a plurality of row-specific addressable first poration sub-electrodes 396.

One experimental embodiment includes an electrostatic gun for injecting DNA into cells and for sorting cells according to size. The embodiment includes an array of conical horn structures or pyramidal passages. Each horn structure includes a pair of spaced-apart electroporation electrodes that apply a potential across cell membranes. Each horn structure opens to an orifice that has a diameter corresponding to a target cell size. Behind each horn structure is a piezoelectric transducer that provides an ultrasonic pressure wave to transport analyte and enhance poration (via sonoporation).

The device provides on-demand DNA delivery in or out of the cell via combination (or possibly individual action) of ultrasonic and electrical poration or lysis, respectively, of the cell membrane. In addition to poration and lysing functionality, the device also includes the capability for inline size selective cell sorting (via control of the ejector nozzle size) prior to poration/lysis. It also enables transport of modified cell/DNA to final destination as a post-poration/lysis step for further processing. The device can operate in both high-throughput and multiplexed mode in the microarray format.

The electro-sonic DNA gun is designed to work in an array format, so it can operate in both high throughput mode, and also in the multiplexed mode if the array is divided into individually controlled compartments. Each compartment is loaded with an analyte that contains a buffer solution, suspension of biological cells, and a DNA transport that one desires to inject into the cells. Different analytes may be loaded into different compartments. The horn nozzle structures of the analyte loaded chambers efficiently focus acoustic waves generated by driving the piezoelectric transducer at one of the resonant frequencies of the fluid cavities, leading to establishment of a significant pressure gradient near the tip of the nozzles. This pressure gradient at the nozzle tip serves two important functions: (1) it allows to eject on-demand droplets of the analyte from the device into the cell; and (2) it allows strong and limited duration application of mechanical force to the cell membrane as it passes through the nozzle neck during the ejection, leading to either membrane poration and injection of DNA and RNA from the solution into the cell through open pores or cell membrane rupture (lysis) and release of the cell content into the buffer solution. In both cases, a drop, containing buffer solution together with either a cell injected with DNA or DNA released from the lysed cell is being ejected and could be delivered to the specific location or destination point for further processing. Efficient sonoporation occurs when amplitude of the acoustic pressure pulse applied to the cell membrane is between 1 and 100 kPa (in access of the DC hydrostatic pressure) and the pulse duration in the range of 0.1 and 10 μs—these operating parameters are readily realized in operation of the electro-sonic DNA gun by varying an amplitude and modulating frequency of the piezoelectric transducer driving frequency.

Simultaneously with acoustic pumping, cell poration (for DNA injection) or rupture (for DNA extraction) can be accomplished via application of AC or DC electric field to the electroporation electrodes deposited within the nozzles of the device fluid chambers. Because of the close proximity of electrodes (separation distance ranging from 10 μm to 100ths of a micrometer) fairly small voltages of the order of 1 to 10 Volts are needed to achieve electric field strengths of 1 kV/cm required for electroporation. Typical electric signal pulse length required for electroporation is between 100 ns and 100 μs, and is readily realized by the disclosed electro-sonic DNA gun when operated in either MHz frequency range or in kHz domain by using time-domain amplitude modulation of the driving signal. Finally, since the size of the droplets that can be ejected from the device is dictated by the size of the nozzle orifice, it allows for cell separation and sorting through size exclusion immediately after DNA injection and extraction. The size of the realized nozzles (3 to 30 μm) corresponds well with the size of eukaryotic animal cells (typically 5-30 μm; for example, red blood cells are ~7-9 μm and mammalian cells are 8-20 μm in diameter), making the size-based separation realizable.

The device is capable of delivering a combined action of (1) sonoporation, (2) electroporation, (3) cell separation/sorting via size exclusion, and (4) post-processing cell/DNA transport. Using these multiple functions, two complimentary modes of operation can be achieved in microfluidic format:

Mode 1 (Material Extraction via Cell Lysis)—In this mode the material is being extracted from the cell by lasing (rupturing) cell membrane by applying mechanical (acoustic) and/or electrical force, separately or in combination, of the magnitude and duration greater than certain threshold values. The threshold values are determined by calibrating the system.

Mode 2 (Material Incorporation via Cell Poration)—In this mode the material is being injected into the cells by opening the pores of the cell membrane by applying mechanical (acoustic) and/or electrical force, separately or in combination, of the magnitude and duration greater than certain threshold values required for cell sono-and electro-poration of the cell membrane, but less than the threshold values leading to cell lysis, in accordance with the disclosure provided.

This technology is suited for intercellular drug/biomolecule delivery in pharmaceutical, biotech, and clinical applications. Advantages of the technology include:

Combined mechano (sono-) and electro-poration actions.
Individual control of transfection on a single-cell level.
Simultaneous size-sorting of transfected cells and transport.
High throughput & multiplexed operation in microarray format.
Small sample volumes & both continuous and discrete operation.
Low cost MEMS batch fabrication leading to disposable devices.

The technology has been demonstrated in the laboratory using fluorescent markers and mammalian cells. To date, through the proof-of-concept experimental studies, we have unambiguously demonstrated the electrosonic MEMS gun capability for:

Controllable array operation in drop-on-demand (DOD) mode desirable for high efficiency cellular transfection.
Low power (<100 mW) and temperature (<30° C.) sample ejection without device clogging by biomolecules/cells and with proven thermal stability of operation.
Flow cytometry results unambiguously indicate that biological cells remain alive upon processing by the electrosonic MEMS gun.
Flow cytometry results unambiguously indicate that biological cells are able to uptake foreign molecules (e.g., calcein green fluorescent dye, which do not penetrate the cell membrane under normal conditions) from the surrounding environment upon ejection by the electrosonic gun. Thus, use of the electrosonic gun enables cell treatment which has drug and RNA/DNA/gene delivery potential.
These very promising and significant preliminary results support the credibility of our approach. Work is on-going to optimize the operating parameters and device design as well as to test transfection of different cell-biomolecule combinations.

In one experimental embodiment, an electrosonic DNA gun, according to one embodiment of the invention, was outfitted with an array of 225 nozzles with each hole diameter about 35 micrometers. To avoid overheating of piezoelectric transducer, a pulsing waveform was used with a 2-6% duty cycle, 980 kHz driving frequency, and 10 Hz repetition rate. Three cell samples were analyzed using flow cytometer to determine viability and transfection and uptake efficiency of the device.

A first sample, used for a control experiment, used NIH 3T3 mammalian cells that were used in characterizing device performance and were suspended in a DMEM medium. Propidium iodide (red fluorescent marker) was then added 10 minutes before cytometry analysis in order to stain dead cells. The average cell diameter in suspension was about 15 micrometers.

In a second sample used for a viability experiment, an aqueous solution containing cells were ejected by the DNA gun with the flow rate of about 100 microliters per minute. Approximately 2 ml of the sample was processed by the device and collected for cytometry analysis. The cells were then suspended in DMEM medium, propidium iodide (red fluorescent marker) was added 10 minutes before cytometry analysis in order to stain dead cells.

In a third sample used for a transfection/uptake experiment, calcein (a green fluorescent marker) was added to cell suspension prior to ejection by the DNA gun. Under normal conditions calcein does not penetrate the cell membrane, i.e., it cannot be incorporated into living cells, so it can be used to analyze transfection/uptake efficiency of the device. An aqueous cell suspension containing calcein was ejected by the DNA gun. The sample was collected during 15 minutes of active ejection. The collected sample rested for 10 minutes, then cells were centrifuged and the medium was changed to calcein-free one (through washing). After that the propidium iodide (red fluorescent marker) was added 10 minutes before cytometry analysis in order to stain dead cells.

These experiments demonstrated the following outcomes:

Ejection: Biological cells were successfully ejected by the device without clogging.

Viability: Biological cells were shown to remain alive after being ejected by the device.

Transfection: Biological cells were shown to uptake foreign molecules (i.e., calcein green fluorescent dye) from the external environment, which do not penetrate the cell membrane under normal conditions.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A method of injecting a substance into a living cell having a cell membrane, comprising the steps of:
   a. placing the substance, the cell and a liquid into a tapering passage; and
   b. applying an energy to the cell sufficient to induce poration of the cell, wherein the step of applying an energy to the cell, comprises applying an acoustic pressure wave to the liquid, thereby inducing sonoporation in the cell wherein the tapering passage includes a narrow end that defines an opening passing therethrough, wherein the method further comprises the step of forcing the cell through the opening so that as the cell passes through the opening the cell membrane allows the substance to pass therethrough.

2. The method of claim 1, wherein the step of applying an acoustic pressure wave further comprises the step of forming a standing wave within the tapering passage.

3. The method of claim 1, wherein the acoustic wave comprises an ultrasonic wave.

4. The method of claim 1, wherein the step of applying an energy to the cell comprises the step of focusing the energy within the tapering passage, thereby applying a highly localized energy gradient to the cell.

5. The method of claim 1, wherein the substance comprises genetic material.

6. The method of claim 1, wherein the substance comprises a predetermined chemical composition.

7. The method of claim 1, further comprising the step of applying an electric field to the cell, thereby inducing electroporation in the cell.

8. The method of claim 7, wherein the step of applying an electric field to the cells comprises applying an oscillating electric field.

9. A method of injecting a substance into a living cell having a cell membrane, comprising the steps of:
   a. placing the substance, the cell and a liquid into a tapering passage; and
   b. applying an oscillating electric field to the cell, thereby inducing electroporation in the cell to the cell sufficient to induce poration of the cell; and
   c. applying an acoustic pressure wave to the liquid, thereby inducing sonoporation in the cell.

10. The method of claim 9, wherein the step of applying an acoustic pressure wave further comprises the step of forming a standing wave within the tapering passage.

11. The method of claim 9, wherein the acoustic wave comprises an ultrasonic wave.

12. The method of claim 9, wherein the step of applying an energy to the cell comprises the step of focusing the energy within the tapering passage, thereby applying a highly localized energy gradient to the cell.

13. The method of claim 9, wherein the substance comprises genetic material.

14. The method of claim 9, wherein the substance comprises a predetermined chemical composition.

* * * * *